United States Patent
de Haan et al.

(10) Patent No.: US 10,155,955 B2
(45) Date of Patent: Dec. 18, 2018

(54) **TOMATO PLANTS RESULTING FROM THE INTROGRESSION OF A TRAIT FROM *SOLANUM PENNELLII* INTO *S. LYCOPERSICUM* AND HAVING AN INCREASED YIELD**

(71) Applicant: Monsanto Invest B.V., Bergschenhoek (NL)

(72) Inventors: Anita Afke de Haan, Bleiswijk (NL); Marleen van Luijk, Berkel en Rodenrijs (NL); Bram Rozier, Zwijndrecht (NL)

(73) Assignee: Monsanto Invest B.V., Bergschenhoek (NL)

( * ) Notice: Subject to any disclaimer, the term of this patent is extended or adjusted under 35 U.S.C. 154(b) by 144 days.

(21) Appl. No.: 15/211,980

(22) Filed: Jul. 15, 2016

(65) Prior Publication Data

US 2017/0037423 A1   Feb. 9, 2017

Related U.S. Application Data

(62) Division of application No. 13/377,913, filed as application No. PCT/NL2010/050373 on Jun. 17, 2010, now Pat. No. 9,414,553.

(30) Foreign Application Priority Data

Jun. 17, 2009 (EP) ..................................... 09163015

(51) Int. Cl.
| | |
|---|---|
| *A01H 5/08* | (2018.01) |
| *C12N 15/82* | (2006.01) |
| *A01H 6/82* | (2018.01) |
| *C12Q 1/6895* | (2018.01) |
| *A01H 1/04* | (2006.01) |

(52) U.S. Cl.
CPC ........... *C12N 15/8261* (2013.01); *A01H 1/04* (2013.01); *A01H 5/08* (2013.01); *A01H 6/825* (2018.05); *C12Q 1/6895* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 2007/0300314 A1* | 12/2007 | van Kan | ................ | A01H 1/04 800/265 |
| 2009/0126037 A1* | 5/2009 | Finkers | .............. | C12N 15/8282 800/265 |

FOREIGN PATENT DOCUMENTS

WO    WO 2009/021545    8/2007

OTHER PUBLICATIONS

Alseekh et al., Trends in Plant Science, vol. 18, Issue 10, Oct. 2013, pp. 536-538.*
Wang et al., Molecular Breeding, Apr. 2007, vol. 19, No. 3, pp. 209-214.*
Zou et al., Plant Science, Jan. 2006, vol. 170, No. 1, pp. 120-127.*
Kohler et al., Journal of Economic Entomology, Jun. 2005, vol. 98, No. 3, pp. 988-995.*
Frary et al.,Theoretical and Applied Genetics, Jul. 2005, vol. 111, No. 2, pp. 291-312.*
Causse et al., Journal of Experimental Botany, Aug. 2004, vol. 55, No. 403, pp. 1671-1685.*
Martin et al., Crop Science, Nov.-Dec. 1999, vol. 39, No. 6, pp. 1775-1783.*
Foolad et al., Plant Cell Reports, Feb. 1998, vol. 17, No. 4, pp. 306-312.*
McNally et al., Molecular Breeding, 1997, vol. 3, No. 3, pp. 203-212.*
Mutschler et al., Theoretical and Applied Genetics, 1996, vol. 92, No. 6, pp. 709-718.*
Barr et al., "The Ghost Terminal Oxidase Regulates Developmental Programming in Tomato Fruit," *Plant, Cell and Environment*, 27:840-852, 2004.
Carmel-Goren et al., "The Self-Pruning Gene Family in Tomato," *Plant Molecular Biology*, 52:1215-1222, 2003.
Eshed et al., "An Introgression Line Population of Lycopersicon Pennellii in the Cultivated Tomato Enables the Identification and Fine Mapping of Yield-Associated QTL," *Genetics*, 141:1147-1162, 1995.
Frary et al., "Advanced Backcross QTL Analysis of Lycopersicon Esculentum x. L. Pennellii Cross and Identification of Possible Orthologs in the Solanaceae," *Theor Appl Genet*, 108:485-496, 2004.
Liu et al., "There is more to Tomato Fruit Colour Than Candidate Carotenoid Genes," *Plant Biotechnology Journal*, 1:195-207, 2003.
Peralta et al., "Granule-boud startch synthase (GBSSI) gene phylogeny of wild tomatoes (*Solanum L.* section *Lycopersicon* [Mill.] Wettst. Subsection *Lycopersicon*)," *American Journal of Botany*, 88(10):1888-1902, 2001.
Schauer et al., "Comprehensive Metabolic Profiling and Phenotyping of Interspecific Introgression Lines for Tomato Improvement," *Nature Biotechnology*, 24(4):447-454, 2006.

(Continued)

*Primary Examiner* — Phuong T Bui
(74) *Attorney, Agent, or Firm* — Dentons US LLP

(57) ABSTRACT

The present invention provides a method for the production of *S. lycopersicum* plants having an average sympodial index of 2 and producing red-colored fruits comprising crossing a plant of *S. lycopersicum* capable of producing red-colored fruits, with a plant of a *Solanum* spp. having an average sympodial index of 2, collecting the seeds resulting from the cross, regenerating the seeds into plants, providing one or more backcross generations, selfing the backcross plants, growing the selfed seed into plants, and identifying and selecting plants having an average sympodial index of 2 and producing red-colored fruits.

20 Claims, 7 Drawing Sheets
Specification includes a Sequence Listing.

(56) References Cited

OTHER PUBLICATIONS

International Search Report and Written Opinion regarding International Application No. PCT/NL2010/050373, dated Dec. 10, 2010.
International Preliminary Report on Patentability regarding International Application No. PCT/NL2010/050373, dated Dec. 20, 2011.
Rick, "Inheritance of sympodial index," *Report of the Tomato Genetics Cooperative* vol. 36, Apr. 1986.
International Union for the Protection of New Varieties of Plants, "Explanatory Notes on the Definition of Variety Under the 1991 Act of the UPOV Convention," Oct. 21, 2010, Geneva.

* cited by examiner

Figure 1

MPRERDPLVVGRVVGDVLDPFTRTIGLRVIYRDREVNNGCELRPSQVINQPRVEVGGDDL
RTFFTLVMVDPDAPSPSDPNLREYLHWLVTDIPATTGSSFGQEIVSYESPRPSMGIHRFV
FVLFRQLGRQTVYAPGWRQNFNTRDFAELYNLGLPVAAVYFNCQRESGSGGRRRSAD

MSVALLWVVS PCDVSNGTSF MESVREGNRF FDSSRHRNLV SNERINRGGG KQTNNGRKFS
VRSAILATPS GERTMTSEQM VYDVVLRQAA LVKRQLRSTN ELEVKPDIPI PGNLGLLSEA
YDRCGEVCAE YAKTFNLGTM LMTPERRRAI WAIYVWCRRT DELVDGPNAS YITPAALDRW
ENRLEDVFNG RPFDMLDGAL SDTVSNFPVD IQPFRDMIEG MRMDLRKSRY KNFDELYLYC
YYVAGTVGLM SVPIMGIAPE SKATTESVYN AALALGIANQ LTNILRDVGE DARRGRVYLP
QDELAQAGLS DEDIFAGRVT DKWRIFMKKQ IHRARKFFDE AEKGVTELSS ASRFPVWASL
VLYRKILDEI EANDYNNFTK RAYVSKSKKL IALPIAYAKS LVPPTKTASL QR

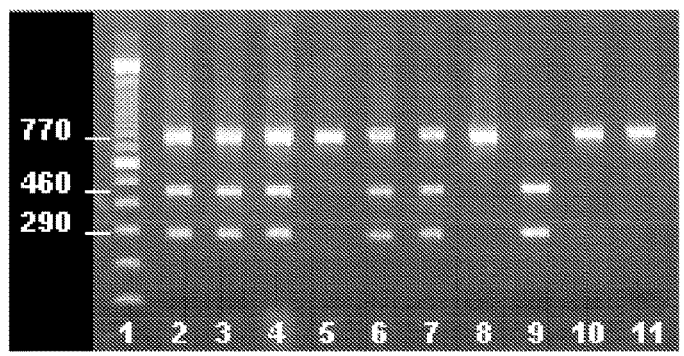

Sequence spi^2

AGGAGATGACCTACGTACCTTTTTCACTTTGGTAATATTTCTTATATTTTTGTTTGGGAATATAATTAAG
TTATTATTTCTATGATTTTCATAAGCAAAGTAAAAAGTATTTTTGTCTTTTTGTAAAGGTTATGGTGGACC
CTGATGCTCCAAGTCCGAGTGATCCAAATCTGAGAGAATACCTTCACTGGTCCGTATTTTTCCTTATTCTC
TCTTCTTTTTAATCTCTTTCTTTTTTGACCTTTTCACTTTCCCATAATAATTATATTCTTTAGTAATTATA
TATCCTTTTATTTTATTTTTAAAAATTGGAAAGGAGAAACGAAGAGGAGATTTTTACATGTGAGGGATTTA
ATTGTAATGCAAATGGTAGAAATATATAAATGTGAAGATATATTCTTGAACTTAAAAACAAACTACTAAAA
TAAAAATGAATAAAATATTTACTCTGTCAATATTCTGTACTATATTGGTCAATGAATATTTATATTATTCA
TGACTTTAAAAATAGTCAAACCGAGACATAAGGTAAAAGTCAAAATACGTTTAAGCTCATTCATATAAATG
AATATTTTAAATTTTGTTGCATCCATCAAAATATCTACTTTTTAAGAATGATATTTATTTTATAATATTC
ATATTTGATTCGTTGATGGATAGATTTTATTCTGTAAGAAATTAAATAAAAATAAAAATTTAGGCCTAGTC
ATATCCATCTAAAATGGGTGAGATT

Sequence spi^3

GAGGAGATGACCTACGTACCTTTTTCACTTTGGTAATATTTCTTATATTTTTGTTTGGGAATATAGTTAA
GTTGATTTTCATAAGCAAAGTAAAAAGTATTTTTGTCTTTTTGTAAAGGTTATGGTGGACCCTGATGCTCC
AAGTCCGAGTGATCCAAATCTGAGAGAATACCTTCACTGGTCCGTATTTTTCCTTATTCTCTCTTCTTTT
CATCTCTTTCTTTTTTGACCTTTTTACTTAATTATATTCTTTAGTAATAATATATGATGATATCCTTTTTA
AAAATTGGAAATACGAAAAGGAGAAATGAAGAGGAGATTTACATGTGAGGGAGCAGATGGTAGAAATATAT
AAATGTGAAGATATATTCTTGAACTTAAAAACAAGCTACTAAAATAAAAATGAATAAAATATTTACTCT
GTCAATATTCTGTACTATATTGGTCAATGAATATTTATATTATTCATGACTTTAAAAATAGTCAAACGAGA
CATAACGTAAAAGTCAAAATACGTTTAAGCTCATTCATATAAATGAATATTTTTAAAATTTGTTGCATCCA
TCAAAATATCTACTTTTTAAGGAATGATATTTATTTCATAATATTCATATTTGATTCGTTGATGGATAGAT
TTTATTCTTTAAAAAATTAAATAAAAAAAATAAAATTGGCCTAGTCATATCCATCTAAAATGGGTGA

Figure 6

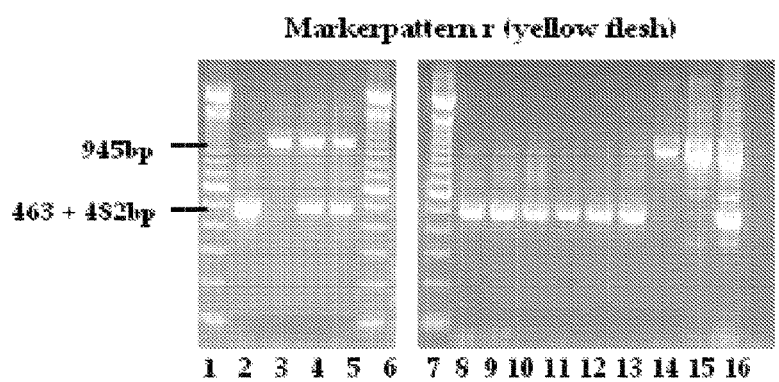

Sequence red color

TCTGGAGAACGGACGATGACATCGGAACAGATGGTCTATGATGTGGTTTTGAGGCAGGCAGCCTTGGTGAA
GAGGCAACTGAGATCTACCAATGAGTTAGAAGTGAAGCCGGATATACCTATTCCGGGGAATTTGGGCTTGT
TGAGTGAAGCATATGATAGGTGTGGTGAAGTATGTGCAGAGTATGCAAAGACGTTTAACTTAGGTTAGCTT
CTTCAATCTATTCATTCGTTTACCAAATATTATTTGGTAAGCACTAATTATGAATATATATATGTTCATGT
TATTGATGAAGACAAAATTTGATCTTTGTTTGTTTATTCAGGAACTATGCTAATGACTCCCGAGAGAAGAA
GGGCTATCTGGGCAATATATGGTGAGGTTTCTAGCCATTTAATAACAGTTACGCGCACAAACACATATGAT
TAATCGGGGACGAGAAAAAAAGAAATGAAGTTTGAGTTTTGAGGGTCATATGTAATAGGTAAATCCGAGCT
TGACTAGCTTGAGATGTTTATTGTCATATCATGCTCAATACTAACCAAAACACTGAAAAAGAACTTGATTA
TATTTACATACTAATATTTTCATTTGCGTTGCTGTTCACATTTTTACCTATGGAACTGGTTTTTGTGATTT
GTTATACTTCATATTCGATGTTAATAAAATATATCATTCCTCCCTTTTTCTCCACTTCAAGCTTTACTGTA
GTGTTGAAAGGGGAAACTCCTTTTAATGATTGCATATATAAACGAACTTCTTGAGTTGAATAGTTTCTCAT
TATGATCTGTT

Sequence yellow color

TCTGGTGAACGGACGATGACATCGGAACAGATGGTCTATGATGTGGTTTTGAGGCAGGCAGCCTTGGTGAA
GAGGCAGCTGAGATCTACCAATGAGTTAGAAGTGAAGCCGGATATACCTATTCCGGGGAATTTGGGCTTGT
TGAGTGAAGCATATGATAGGTGTGGTGAAGTATGTGCAGAGTATGCAAAGACGTTTAACTTAGGTTAGCTT
CTTTAATCTATTCATTTGTTTACCAAATATTATTTGGTAAGCACTAATTATGACTATATATATATATATAT
ATATATATATATATATATATATCTGTTCATGTTATTGATGAAGACAAAATTTGATCTTTGTTTGTTTAT
TCAGGAACTATGCTAATGACTCCCGAGAGAAGAAGGGCTATCTGGGCAATATATGGTGAGGTTTCTAGCCA
TTTAATAACAGATACGCACACAAACACATATGATTAATCGGAGACGAGAAAAAAAGAAATGAAGTTTGAGT
TTGAGGGTCATATATAATAGGTAAATCCGAGCTTGACTAGCTTGAGATGTTTATTGTCATATCATGCTCAA
TACTAACCAAAACACTGAAAAAGAACATGATTATATTTACATACTAATATTTTCATTTGCGTTGCTGTTCA
CATTTTTACCTATGGAACTGGTTTTTTTGATTTGTTATACTTCATATTCGATGTTAATAAACTATATCAT
TCCTCCCTTTTTCTCCACTTCAAGCTTTACTGTAGTGTTGAAAGGGGAAACTCCTTTTAATGATTGCATAT
ATAAACGAACTTCTTGAGTTGAAAAATTTCTCATTATGATCTGTTAAACAGTATG

TOMATO PLANTS RESULTING FROM THE INTRODUCTION OF A TRAIT FROM *SOLANUM PENNELLII* INTO *S. LYCOPERSICUM* AND HAVING AN INCREASED YIELD

CROSS-REFERENCE TO RELATED APPLICATIONS

This application is a divisional of U.S. application Ser. No. 13/377,913, filed Jan. 31, 2012, which issued as U.S. Pat. No. 9,414,553 on Aug. 16, 2016, which application is a National Stage Application under 35 U.S.C. 371 of International Application No. PCT/NL/2010/050373, filed Jun. 17, 2010, which application claims the benefit of European Patent Application Number 09163015.2, filed Jun. 17, 2009, each of the disclosures of which are incorporated herein by reference in their entireties.

FIELD OF THE INVENTION

The present invention is in the field of plant breeding. More in particular, the invention relates to novel tomato plants having improved growth patterns, and to methods for producing such tomato plants using marker assisted breeding tools.

BACKGROUND OF THE INVENTION

Tomatoes (*Solanum* spp.) exhibit sympodial growth. This is a pattern of growth wherein the apical or terminal bud dies or ends in an inflorescence, and growth (sympodial shoots) continues from axillary or lateral buds. What looks like the plant's main axis is actually a series of many lateral branches, each arising from the previous lateral branch. After the production of some leaves by the shoot apical meristem (SAM), the growth of the primary shoot is terminated by the initiation of the first inflorescence, which is displaced from its terminal position by activation of the meristem at the axil of the last initiated leaf. The latter so-called sympodial meristem (SYM) continues shoot growth, carrying up the subtending leaf until it occupies a position above the inflorescence, which then develops laterally. The SYM undergoes a vegetative phase—producing most often three leaves—then initiates the second inflorescence, which is once again displaced laterally by the active outgrowth of the next SYM. The process is indefinitely reiterated and growth is thus indeterminate. The shoot section between two successive inflorescences is called the sympodium, and the number of leaf nodes per sympodium is referred to as the sympodial index (spi).

Thus, vegetative and reproductive phases alternate regularly during sympodial growth in tomato. In wild-type 'indeterminate' plants, inflorescences are separated by three vegetative nodes. As a result of this pattern of growth, a distinctive feature of tomato is its spi value. All of the red-fruited species such as *S. lycopersicum* have a mean spi of 3, whilst all green-fruited spp., including *S. pennellii*, have an average spi of 2. The spi is therefore related to fruit color and is species-specific.

Of all tomato species, *S. lycopersicum* (formerly *L. esculentum*) is the only commercially valuable species, due to its appealing and tasty fruits.

SUMMARY OF THE INVENTION

In an attempt to solve the problem of improving yield in tomato, the present inventors have now recognized that it would be desirous to produce *S. lycopersicum* plants for protected cultivation (i.e. greenhouse growth) with a spi of 2 (herein after referred to by the designation spi^2), thereby increasing the density of trusses along its shoot.

In an attempt to produce a spi^2 *S. lycopersicum* line, *S. pennellii* LA716 (PI 24650) was back-crossed to a proprietary *S. lycopersicum* breeding line. LA716 is a self-fertile, homozygous green fruited, indeterminate accession collected in Atico, Peru and obtainable from the Tomato Genetics Stock Centre, University of California, Davis (U.S.A.). During backcrossing, selection for the spi^2 trait was difficult due to the fact that the spi was very variable.

In two segregating populations, it was found that the SP3D gene (AY186735, 6819 bp) was fully linked with the spi variation. Plants with SP3D homozygous for the donor LA716, gave on average 2.1 leaves between subsequent inflorescences. Heterozygous plants or plants homozygous for the *S. Lycopersicum* allele, gave higher number of leaves between fruit clusters. The linkage between the marker and the trait was 100% in the studies performed.

The inventors thus discovered that it is possible to produce spi^2 *S. lyeopersicum* plants by crossing a plant of a *S. lyeopersicum* line with a plant of a green-fruited tomato such as *S. pennellii*. Moreover, the present inventors discovered that the production of additional *S. lyeopersicum* lines with spi^2 can be accelerated by using newly discovered markers for the spi^2 trait. It is expected that the spi^2 trait in other *Solanum* spp. is also linked to the SP3D gene. Hence, suitable markers for other spi^2 donor plants can be developed by the skilled person. It is therefore contemplated in the context of the present invention that spi^2 *S. lyeopersicum* plants can be produced by similar methods using other spi 2 *Solanum* species as donor plants, and using a marker based on polymorphic sequences in the SP3D gene of the donor plant.

During backcrossing studies with the newly developed spi marker it was found that the spi^2 trait was coupled to yellow fruit color. Plants homozygous for the *S. pennellii* allele spi^2 produced yellow fruits.

It was however discovered that the traits for spi^2 and fruit color could be uncoupled. In the segregating population several plants were discovered that combined spi^2 with red fruit color. However, in many cases, selfing of these plants resulted in segregation for fruit color. It proved virtually impossible to select the homozygous spi^2 combined with homozygous red color genotypes based on phenotypic characteristics. This greatly hampers successful breeding for spi^2 and red color in commercial varieties.

In search for a suitable marker to allow for detecting the uncoupling of the spi and color traits in segregating populations, the inventors discovered that the gene for phytoene synthase (PSY-1 X60441.1) was linked to SP3D in *S. pennellii*. Hence, the possibility to use this gene as a marker for uncoupling the spi and color trait was investigated. It was subsequently found that a marker based on the sequence polymorphisms between the phytoene synthase gene in *S. pennellii* and in *S. lycopersicum* proved a very robust marker system for the development of red fruited, spi^2 *S. lycopersicum* lines.

Thus, the present invention in one embodiment provides a method for producing a spi^2 *S. lycopersicum* plant comprising a step of marker assisted selection using a marker linked to the family of the spi genes and/or a marker linked to a gene from the carotenoid synthesis pathway. Using this method, plants with a low spi that bear red fruits can be produced. It was hitherto unknown that spi and fruit color were intricately linked and could be uncoupled. In fact, this problem has not been addressed in the prior art.

Now in a first aspect, the present invention provides a method for the production of an indeterminate or semi-determinate *S. lycopersicum* plant having a sympodial index of between 1.6 and 2.4, preferably 1.8 and 2.2, and producing red-colored fruits, said method comprising:

a) crossing a plant of a recipient breeding line of an indeterminate or semi-determinate *S. lycopersicum* capable of producing red-colored fruits, with a plant of a donor line of a *Solanum* spp. having a sympodial index of between 1.6 and 2.4, preferably 1.8 and 2.2;

b) collecting the seeds resulting from the cross in step (a), c) regenerating the seeds into plants;

d) providing one or more backcross generations by crossing the plants of step (c) or (optionally selfed) offspring thereof with one or more plants of said recipient breeding line of *S. lycopersicum* to provide backcross plants;

e) selfing plants of step (d) and growing the selfed seed into plants;

f) optionally repeating said steps of backcrossing and selfing of steps (d) and/or (e);

g) identifying and selecting from the plants grown in step (c), (e) or (f) plants having a sympodial index of between 1.6 and 2.4, preferably 1.8 and 2.2, and producing red-colored fruits.

In a preferred embodiment of said method, the step of identification and selection of step g) is performed by marker-assisted selection.

The breeding line of an indeterminate or semi-determinate *S. lycopersicum* is preferably a line with a yellow (non-transparent) skin.

The breeding line of an indeterminate or semi-determinate *S. lycopersicum* is preferably a cherry tomato, a cherry truss tomato or a cocktail tomato.

The breeding line of *S. lycopersicum* is preferably a line possessing resistance to tobacco mosaic virus (TMV).

The donor line is preferably not a line of *Solanum pimpinellifolium*.

The step of marker-assisted selection in a method of the invention preferably comprises the use of a marker linked to the SP3D gene, and/or a marker linked to the PSY1 gene.

A suitable donor line of a *Solanum* spp. having a sympodial index of between 1.6 and 2.4, preferably 1.8 and 2.2, is the wild tomato species *S. pennellii* (LA716), which is available from the Tomato Genetics Resource Center (TGRC), Department of Plant Sciences, University of California, Davis, USA.

It is contemplated that also other genes than the SP3D gene that are linked to the spi^2 trait can suitably be used as a basis for designing suitable markers for selection purpose. In general, it is envisioned by the present inventors that suitable genes linked to the spi^2 trait may be selected from the gene family for self pruning genes, including SP2G, Genbank accession No. AY186734; SP3D, Genbank accession No. AY186735; SP5G, Genbank accession No. AY186736; SP6A, accession No. AY186737; and SP9D, Genbank accession No. AY186738. Markers based on said genes may comprise 20-30 or larger nucleotide fragments of said genes It is contemplated that also other genes than the PSY1 gene that are linked to the color trait can suitably be used as a basis for designing suitable markers for selection purpose. In general, it is envisioned by the present inventors that any gene (or fragment thereof) linked to fruit color is suitable for use as a marker. However, since the coupling between the spi and color traits, fruit color genes that are in coupling phase with a gene from the family of self-pruning genes are preferred. Genes encoding enzymes in the carotenoid synthesis pathways (the 1-deoxy-D-xylulose-5-phosphate (DOXP) isoprenoid biosynthetic pathway in plastids) are in principle also suitable. These include phytoene synthases (PSY1, Genbank accession no. EF157835.1 and PSY2, Genbank accession no. EU021055.1), phytoene desaturase (PDS, Genbank accession no. X71023.1), zeta-carotene desaturase (ZDS, Genbank accession no. AF195507.1), and carotene isomerase (CRTISO). Phytoene synthases such as PSY1, PSY2 and LOC778345 (accession no. DQ335097.1) are however preferred, as markers based on these genes (or fragments thereof) have provided very good association and result in proper selections. Again, markers based on said genes may comprise 20-30 or larger nucleotide fragments of said genes. The accession numbers indicated above refer to the Genbank entries in the database version of June 2009.

Contemplated as being suitable for use in aspects of the invention are markers having nucleic acid with at least 80%, more preferably at least 90% sequence identity to the sequences of the genes indicated above, as well as markers capable of hybridizing under stringent conditions to the genes indicated above, or to their complementary strands.

Thus, desirable recombinant plants may be found by using markers based on the gene sequences linked to spi^2 and based on the gene sequences linked to fruit color.

In another aspect, the present invention provides a plant of a *S. lycopersicum* breeding line having an average sympodial index of between 1.6 and 2.4, preferably 1.8 and 2.2, and producing red-colored fruits. The term breeding line as used herein refers to an elite line having amongst other beneficial traits multiple disease and/or pest resistance traits and high yielding fruit production characteristics, and generally refers to a plant used as a parent in the production of commercial hybrid plants used to produce marketable tomato fruits.

A plant of the invention is preferably a recombinant plant. The plant of the invention preferably comprises an introgression from a plant of a donor line of a *Solanum* spp. having an average sympodial index of between 1.6 and 2.4, preferably 1.8 and 2.2, said introgression comprising genes that result in an average sympodial index of between 1.6 and 2.4, preferably 1.8 and 2.2, in the recipient plant. Said donor plant may suitably be a plant of the wild tomato species *S. pennellii*, preferably *S. pennellii* LA716.

The plants of the invention preferably exhibit higher yields than plants of the breeding line lacking the introgression responsible for the spi^2 trait. Preferably, the total fruit weight per plant is increased by at least 3-5%, more preferably by at least 10%, still more preferably by at least 20, 30, 40, or even 50% relative to a plant of said tomato breeding line lacking said introgression.

A plant of the present invention is in one embodiment obtained by a method of producing a plant as described herein.

Yield per plant is generally dependent on the type of tomato, the planting density and the number of stems per plant. A good grower may reach yields that are 10% above average. At an average planting density of 2.3 plants/m$^2$, and a single stem per plant, the yield for a small fruited truss or cluster tomato is generally about 57-58 kg/m$^2$/yr; the yield for a cherry tomato is generally about 40 kg/m$^2$/yr; the yield for a beef tomato is generally about 60 kg/m$^2$/yr; and the yield for a large fruited truss or cluster tomato is generally about 60-65 kg/m$^2$/yr. Hence it is preferred that yields for the tomatoes of the invention are at least 10-15% higher than these standard yields.

It is an important advantage of the plants of the invention that the picking of leaves is no longer necessary. S. lycopersicum plants with an average spi^3 require manual removal of on average 1 leaf per sympodium in order to optimize productivity. This is no longer necessary when using the plants of the invention as production crop.

Other aspects of the invention include fruit of a plant according to the invention described above as well as seed harvested from said plant.

The present invention also contemplates the use of the markers as described herein for selecting the spi^2 trait in tomato plants, and for monitoring the uncoupling between yellow fruit color and spi^2 in crossings between S. lycopersicum and wild tomato species, such as S. pennellii.

The invention further provides the use of a polymorphic sequence of the SP3D gene of L. esculentum as a marker for the sympodial index.

DESCRIPTION OF THE FIGURES

FIG. 1 shows the complete amino acid sequence of the protein product of the Solanum lycopersicum SP3D (SP3D) gene (GenBank accession AY186735) (SEQ ID NO:1).

Figure 2:
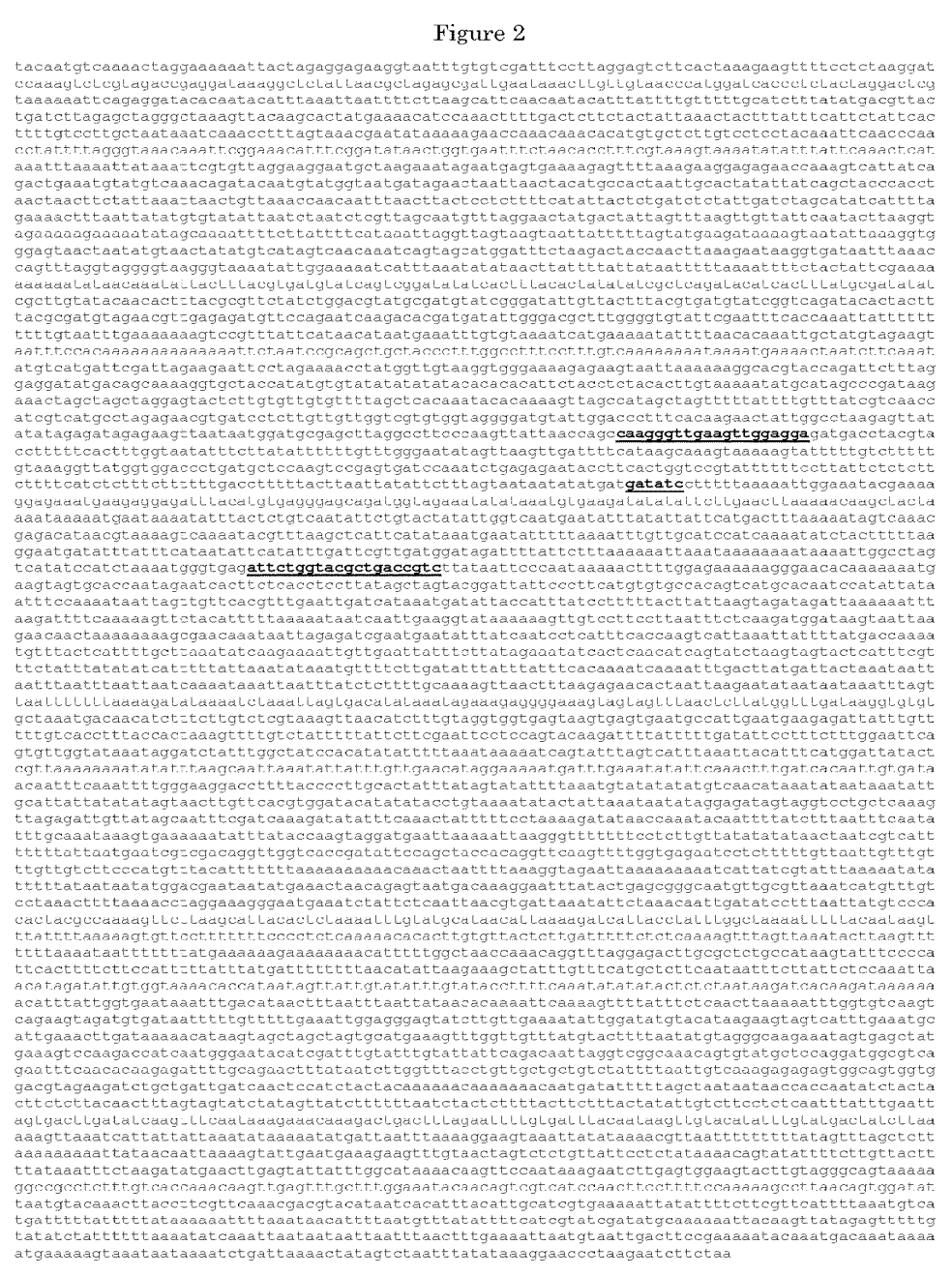

FIG. 2 shows the complete nucleotide sequence of the Solanum lycopersicum SP3D (SP3D) gene (GenBank accession AY186735) (SEQ ID NO:2). Underlined is the approximate position of the CAPS marker indicated herein showing, respectively, the forward primer binding site (5'-caagggttgaagttggagga) (SEQ ID NO:3), the restriction site for EcoRV (5'-gatatc) and the reverse primer binding site (5'-attctggtacgctgaccgtc) (SEQ ID NO:4).

FIG. 3 shows the complete amino acid sequence of Solanum lycopersicum phytoene synthase (Psy1) protein (GenBank accession ABM45873.1) (SEQ ID NO:5).

Figure 4:
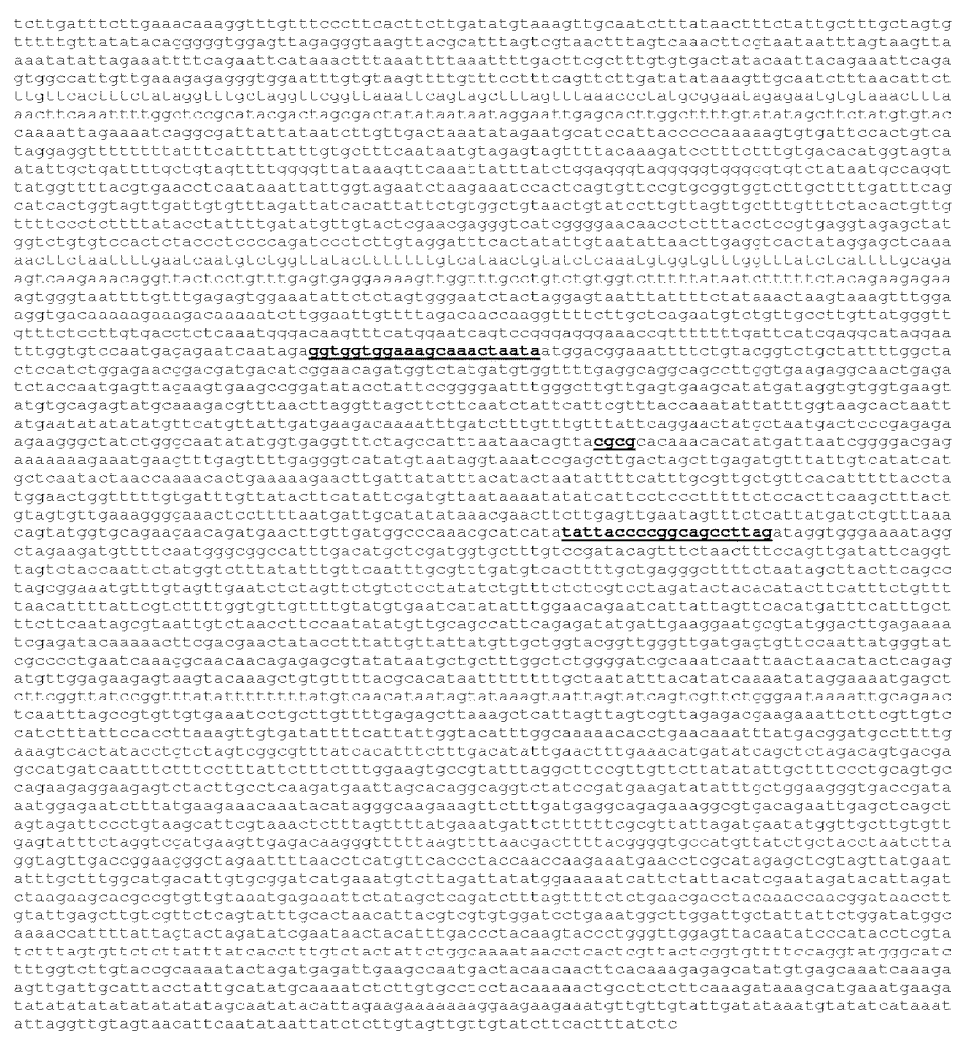

FIG. 4 shows the complete nucleotide sequence of the Solanum lycopersicum phytoene synthase (Psy1) gene (GenBank accession EF157835) (SEQ ID NO:6). Underlined is the approximate position of the CAPS marker indicated herein showing, respectively, the forward primer binding site (5'-ggtggtggaaagcaaactaata) (SEQ ID NO:7), the restriction site for EcoRV (5'-cgcg) and the reverse primer binding site (5'-tattaccccggcagccttag) (SEQ ID NO:8).

FIG. 5 shows the result of the spi^2 marker selection. Lane 1=100bp ladder (the bright band is 600 bp); Marker associated with spi^2=lane 9; Marker associated with heterozygous genotype=lanes 2, 3, 4, 6 and 7; Marker associated with spi^3=lanes 5, 8, 10 and 11. Depicted are also Sequence spi^2 (SEQ ID NO:9) and Sequence spi^3 (SEQ ID NO:10).

FIG. 6 shows the result of the red fruit color marker. Lane 1, 6, 7=100bp ladder (the bright band is 600bp) Score red fruit color=lanes 2, 8, 9, 10, 11, 12, 13; Score heterozygous=lanes 4, 5, 16; Score yellow skin color=lanes 3, 14, 15. Depicted are also Sequence red color (SEQ ID NO:11) and Sequence yellow color (SEQ ID NO:12).

DETAILED DESCRIPTION OF THE INVENTION

Figure 7:
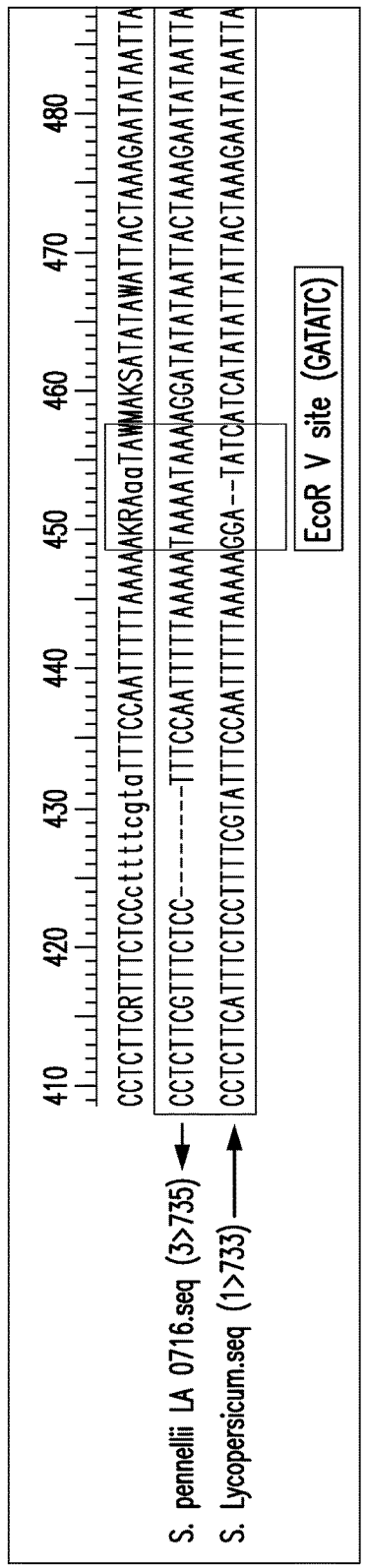
FIG. 7 shows the location of the restriction site in the CAPS marker for spi^2. The consensus sequence at the top of the figure is provided as SEQ ID NO:13; the Solanum pennellii sequence in the middle is SEQ ID NO:14, and the Solanum lycopersicum sequence at the bottom is SEQ ID NO:15.

As used herein, the term "tomato" means any plant, line or population formerly known under the genus name of Lycopersicon including but not limited to Lycopersicon cerasiforme, Lycopersicon cheesmanii, Lycopersicon chilense, Lycopersicon chmielewskii, Lycopersicon esculentum (now Solanum lycopersicum), Lycopersicon hirsutum, Lycopersicon parviflorum, Lycopersicon pennellii, Lycopersicon peruvianum, Lycopersicon pimpinellifolium, or Solanum lycopersicoides. The newly proposed scientific name for Lycopersicon esculentum is Solanum lycopersicum. Similarly, the names of the wild species may be altered. L. pennellii has become Solanum pennellii, L. hirsutum may become S. habrochaites, L. peruvianum may be split into S. 'N peruvianum' and S. 'Callejon de Huayles', S. peruvianum, and S. corneliomuelleri, L. parviflorum may become S. neorickii, L. chmielewskii may become S. chmielewskii, L. chilensemay become S. chilense, L. cheesmaniae may become S. cheesmaniae or S. galapagense, and L. pimpinellifolium may become S. pimpinellifolium (Solanacea Genome Network (2005) Spooner and Knapp; sgn.cornell.edu/help/about/solanum_nomenclature.html).

The term "S. lycopersicum", as used herein, refers to any variety or cultivar of the garden tomato.

The term "sympodial index", as used herein, refers to the number of leaf nodes per sympodium (i.e., between successive inflorescences).

The term "average sympodial index", as used herein, refers to the mean number of leaf nodes per sympodium for all plants in a population, generally the arithmetic average of all values for the population. This figure is preferably around 2 for plants of the present invention.

The term "red-colored fruits", as used herein, refers to fruits having red color (e.g. as determined by visual inspection), including those having yellow skin.

Whether a fruit is red colored can be determined by any method available to tone of skill in the art. Several suitable methods include:

1) Determining fruit color phenotype by visual comparison with a standard tomato color chart or comparator (e.g. The Greenery color scale for Tomato Color Stages, The Greenery, 2004, Barendrecht, The Netherlands, wherein "red-colored fruits" as defined herein is a color comparable to the ripening stage of at least the early stage (color no. 8), but preferably later than early stage (color no.>8), and more preferably a color comparable with a ripening stage between no. 9-12; or the USDA Visual Aid TM-L-1 (February 1975) color chart for classification requirements of surface color for tomatoes, USDA, North Highlands, Calif., wherein "red-colored fruits" as defined herein is a color comparable to at least (5) "Light-red", indicating that more than 60% of the surface, in the aggregate, shows pinkish-red or red, but preferably (6) "Red" indicating that more than 90% of the surface, in the aggregate, shows red color.

2) Determining fruit color using L*, a*, b* color readings of the fruit skin and the puree. Measuring color with L*a*b* values is a quantitative way to indicate color. The three coordinates of CIELAB represent the lightness of the color (L*=0 yields black and L*=100 indicates diffuse white; specular white may be higher), its position between red/magenta and green (a*, negative values indicate green while positive values indicate magenta) and its position between yellow and blue (b*, negative values indicate blue and positive values indicate yellow). The possible range of a* and b* coordinates depends on the color space that one is converting from. "Red fruit-color" is indicated by L*a*b* values of L*=38±5%, a*=19±5%, and b*=21±5% for fruit skin and L*=48±5%, a*=23±5%, and b*=21±5% for values for puree; whereas yellow is indicated by L*a*b* values of L*=47±5%, a*=1±5%, and b*=36±5% for fruit skin and L*=64±5%, a*=0±5%, and b*=32±5% for values for puree.

3) Determining fruit color by measuring lycopene content of the fruit; wherein "red fruit-color" is indicated by a lycopene content of at least 5 mg, preferably at least 6 mg or even 7 mg of lycopene/100 g fresh weight, whereas yellow is indicated by <1 mg, preferably <0.75 mg of lycopene/100 g fresh weight. *Lycopersicon pennellii* fruits have undetectable levels of lycopene as expected of this green-fruited species.

The color of the fruit as indicated herein refers to the color of ripe or mature fruits (i.e. at maturity). The term "mature" as used herein means that the contents of two or more seed cavities have developed a jellylike consistency and the seeds are well developed. External color shows at least a definite break from green to tannish-yellow, pink or red color on not less than 10 percent of the surface, preferably on at least 60 most preferably at least 90 percent of the fruit surface.

The term "crossing" as used herein refers to the fertilization of female plants (or gametes) by male plants (or gametes). The term "gamete" refers to the haploid reproductive cell (egg or pollen) produced in plants by meiosis from a gametophyte and involved in sexual reproduction, during which two gametes of opposite sex fuse to form a diploid zygote. The term generally includes reference to a pollen (including the sperm cell) and an ovule (including the ovum). "Crossing" therefore generally refers to the fertilization of ovules of one individual with pollen from another individual, whereas "selfing" refers to the fertilization of ovules of an individual with pollen from the same individual. When referring to crossing in the context of achieving the introgression of a genomic region or segment, the skilled person will understand that in order to achieve the introgression of only a part of a chromosome of one plant into the chromosome of another plant, random portions of the genomes of both parental lines recombine during the cross due to the occurrence of crossing-over events in the production of the gametes in the parent lines. Therefore, the genomes of both parents must be combined in a single cell by a cross, where after the production of gametes from said cell and their fusion in fertilization will result in an introgression event.

The term "recipient", as used herein, refers to the plant or plant line receiving the trait, introgression or genomic segment from a donor, and which recipient may or may not have the have trait, introgression or genomic segment itself either heterozygous or homozygous.

The term "breeding line", as used herein, refers to a line of a cultivated tomato having commercially valuable or agronomically desirable characteristics, as opposed to wild varieties or landraces. In particular, the breeding line is characterized by having an excellent fruit quality (e.g. red fruits with yellow skin) and is preferably resistant to TMV and other diseases. The term includes reference to elite breeding line or elite line, which represents an essentially homozygous, e.g. inbred or doubled haploid, line of plants used to produce F1 hybrids.

As used herein, the term "hybrid" means any offspring of a cross between two genetically unlike individuals, more preferably the term refers to the cross between two (elite) breeding lines which will not reproduce true to the parent from seed.

The term "donor", as used herein, refers to the plant or plant line from which the trait, introgression or genomic segment originates, and which donor may have the trait, introgression or genomic segment itself either heterozygous or homozygous.

The term "seed" as used herein includes all tissues which result from the development of a fertilized plant egg; thus, it includes a matured ovule containing an embryo and stored nutrients, as well as the integument or integuments differentiated as the protective seed coat, or testa. The nutrients in seed tissues may be stored in the endosperm or in the body of the embryo, notably in the cotyledons, or both.

The term "plant", as used herein, refers to the vegetative growth phase essentially consisting of a single shoot, or only a limited number (2, 3, 4, or 5) shoots which produce fruits in order to optimize yield. Tomato suckers, or side shoots, may be maintained to produce additional flowering shoots as long as the main shoot is strong, but side shoots above 2 or 3 are preferably removed, especially in indeterminate plants, as such tomato suckers will compete for nutrients and may result in fruits of smaller size. The term "plant" includes reference to a plant part. The term "plant part" indicates a part of the tomato plant, including single cells and cell tissues such as plant cells that are intact in plants, cell clumps and tissue cultures from which tomato plants can be regenerated. Examples of plant parts include, but are not limited to, single cells and tissues from pollen, ovules, leaves, embryos, roots, root tips, anthers, flowers, fruits, stems shoots, and seeds; as well as pollen, ovules, leaves, embryos, roots, root tips, anthers, flowers, fruits, stems, shoots, scions, rootstocks, seeds, protoplasts, calli, and the like.

The term "regenerating", as used herein, with reference to a tomato plant refers to the formation of a plant that includes a rooted shoot.

The term "backcross", as used herein, refers to The term backcross refers to the crossing an F1 hybrid with one of the original parents. A backcross is used to maintain the identity of one parent (species) and to incorporate a particular trait from a second parent (species). The best strategy is to cross the F1 hybrid back to the parent possessing the most desirable traits. Two or more generations of backcrossing may be necessary, but this is practical only if the desired characteristic or trait is present in the F1.

The term "backcross generation", as used herein, refers to the offspring of a backcrossing.

The term "selfed", as used herein, means self-pollinated and includes the fertilization process wherein both the ovule and pollen are from the same plant or plant line.

The term "offspring", as used herein, refers to any progeny generation resulting from a crossing or selfing.

The term "growing", as used herein, refers to the growth of a plant, a process wherein the plant biomass is increased and which coincides with a progressive development of the plant.

The term "identifying", as used herein, refers to a process of establishing the identity or distinguishing character of a plant, such as exhibiting a certain trait.

The term "selecting", as used herein, refers to a process of picking out a certain individual from a group of individuals, usually based on a certain identity of that individual.

The term "marker-assisted selection", as used herein, refers to the diagnostic process of identifying, optionally followed by selecting a plant from a group of plants using the presence of a molecular marker as the diagnostic characteristic or selection criterion. The process usually involves detecting the presence of a certain nucleic acid sequence or polymorphism in the genome of a plant.

The term "marker", as used herein, refers to refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, cleaved amplified polymorphic sequence (CAPS) markers or isozyme markers or combinations of the markers described herein which defines a specific genetic and chromosomal location.

The term "linked", as used herein, with reference to markers linked to a trait, refers to a marker the presence of which in the genome of the plant coincides with the presence of the trait. Usually the term refers to a genetic marker that falls within the physical boundaries of a genomic region spanned by at least two markers having established LOD scores above a certain threshold thereby indicating that no or very little recombination between these markers and the trait locus occurs in crosses; as well as any marker in linkage disequilibrium to the trait locus; as well as markers that represent the actual causal mutations within the trait locus. The term "linked" is used in its broadest sense and indicates that the marker and the gene are located within a continuous DNA sequence of several centiMorgan. The term is used herein with reference to the linkage between markers and phenotype and refers to a distance of preferably less than 20 cM, preferably less than 10 cM, still more preferably less than 6, 5, 4, 3, 2, or 1 cM.

The term "gene", as used herein, refers to a hereditary unit consisting of a sequence of DNA that occupies a specific location on a chromosome and that contains the genetic instruction for a particular characteristics or trait in an organism. The term "gene" thus refers to a nucleic acid (for example, DNA or RNA) sequence that comprises coding sequences necessary for the production of an RNA, or a polypeptide or its precursor. A functional polypeptide can be encoded by a full length coding sequence or by any portion of the coding sequence as long as the desired activity or functional properties (for example, enzymatic activity, ligand binding, signal transduction, etc.) of the polypeptide are retained. The term "gene" encompasses both cDNA and genomic forms of a gene.

The term "indeterminate", as used herein, refers to a variety that grows in an upright or gangly fashion, producing fruit throughout the growing season, in contrast to a determinate tomato plant, which grows in a more bushy shape and is most productive for a single, larger harvest, then either tapers off with minimal new growth/fruit, or dies.

The term "yellow skin", as used herein, refers to the pigment present in the cell walls of the epidermis of the fruits, in contrast to colorless skin, in which this pigment is absent. Red-colored fruits can have yellow skin.

The term "recombinant", as used herein with reference to a plant refers to a plant carrying a foreign (donor) gene combined, in whole or in part, in recipient genome.

As used herein, the terms "introgression", "introgressed" and "introgressing" refer to both a natural and artificial process, and the resulting events, whereby genes of one species, variety or cultivar are moved into the genome of another species, variety or cultivar, by crossing those species. The process may optionally be completed by backcrossing to the recurrent parent.

The term "*Solanum* spp.", as used herein, refers to tomatoes or other members of the genus, preferably tomato.

The term "total fruit weight per plant", as used herein, refers to the average yield of fruits over a predetermined period of time, such as a harvest period or the lifetime of a plant.

The term "increased by at least 3-5%", as used herein, or comparative expressions, refers to a significant increase in the average values for a plant population, preferably a population of hybrid plants generated from seed.

The term "fruit", as used herein, refers to tomatoes including a tomato product, such as fruit pulp or processed fruit, wherein the cells in the fruit comprise a genome containing the spi^2 gene and/or containing the nucleic acid sequence of markers linked to the spi^2 trait as identified herein.

Producing Plants with Spi^2

Plant breeders and in particular seed companies employ elite breeding lines, generally referred to as "elite lines" to provide a constant quality product. The elite lines are the result of many years of inbreeding and combine multiple superior characteristics such as high yield, fruit quality, and resistance to pests, disease, or tolerance to abiotic stress. The average yield of these elite lines is generally much higher than the original wild (landrace) accessions from which many of the modern tomato varieties are descendants. The elite lines can be used directly as crop plant, but are typically used to produce so-called F1 or single-cross hybrids, produced by a cross between two (homozygous or inbred) elite lines. The F1 hybrids thus combine the genetic properties of the two parents into a single plant. An additional benefit of hybrids is that they express hybrid vigour or heterosis, the poorly understood phenomenon that hybrid plants grow better than either (inbred) parent and show higher yields.

Backcross or pedigree selection is one method by which breeders add desirable agronomic traits to their elite breeding lines. The method involves crossing the breeding line with a line that expresses the desirable trait followed by backcrossing offspring plants expressing the trait to the recurrent parent. As a result, the selection of an individual as a parent in a breeding program is based on the performance of its forebears. Such methods are most effective in breeding for qualitatively-inherited traits, i.e traits which are present or absent.

Recurrent selection is an alternative breeding method for improving breeding lines and involves systematic testing and selection of desirable progeny followed by recombination of the selected individuals to form a new population. Recurrent selection has proven effective for improving quantitative traits in crop plants. Recurrent selection, however, decreases the rate of broadening genetic basis underlying the various traits in a breeding program, and its potential is therefore limited.

The present inventors discovered that the yield of a tomato plant may be increased by introgressing into an elite breeding line the trait of spi^2.

A first method would comprise introgressing the trait from a tomato plant having a sympodial index of about 1.8-2.2, such as a plant of the wild tomato species *S. pennellii*, such as *S. pennellii* LA716, or an offspring plant thereof having said spi, into a plant of a tomato line of interest. This may for instance be achieved by crossing a plant of a recipient breeding line of *S. lycopersicum* capable of producing red-colored fruits, with a plant of a donor line of a tomato species, preferably a *S. lycopersicum* variety, having an average sympodial index of between 1.8 and 2.2. This will result in a situation wherein the spi^2 gene is in the genetic background of the tomato line of interest. The establishment of the proper introgression in offspring plants may be monitored by using specific markers as defined herein.

Recombination is the exchange of information between two homologous chromosomes during meiosis. In a recombinant plant, DNA that is originally present on a specific location within the chromosome is exchanged for DNA from another plant (i.e. maternal for paternal or vice versa). In order to exchange only the required material, and maintain the valuable original information on the chromosome as much as possible, will usually require two crossover events. The normal way to find such a recombinant is to screen a population of F2-plants. This population must be of sufficient size in order to detect the rare (low frequency) double recombinants. The frequency of recombination can be expressed in a genetic distance. For instance, a single recombinant in a 10 cM area can be found with a frequency of 10% (1 centimorgan is defined as 1% recombinant progeny in a testcross).

The present invention also provides methods of producing the plants of the invention using marker assisted selection (MAS). The invention therefore relates to methods of plant breeding and to methods to select plants, in particular tomato plants, particularly cultivated tomato plants as breeder plants for use in breeding programs or cultivated tomato plants for having desired genotypic or potential phenotypic properties, in particular related to producing quantities of valuable tomato fruits, also referred herein to as agronomically desirable plants. Herein, a cultivated plant is defined as a plant being purposely selected or having been derived from a plant having been purposely selected in agricultural or horticultural practice for having desired genotypic or potential phenotypic properties, in particular a plant obtained by inbreeding.

Since the gene can only be properly identified phenotypically when the plant has produced several sympodia, it is of particular advantage that the establishment of the proper introgression in offspring plants may be monitored by using the gene-specific markers as provided herein, either in cis or in trans coupling as explained below. By using marker assisted selection (MAS) or marker assisted breeding (MAB) methods, the skilled person is therefore provided with methods for selecting plants carrying the desired genotype loci and discarding plants lacking the potential of producing spi^2 progeny.

The present invention thus also provides methods for selecting a tomato plant exhibiting a sympodial index of about 2, comprising detecting in said plant the presence of the spi^2 gene as defined herein. In a preferred method of the invention for selecting such a plant the method comprises:

a) providing a sample of genomic DNA from a tomato plant;

b) detecting in said sample of genomic DNA at least one molecular marker linked to the gene for spi^2.

The step of providing a sample of genomic DNA from a tomato plant may be performed by standard DNA isolation methods well known in the art.

The step of detecting a molecular marker (step b) may, in a preferred embodiment, comprise the use of CAPS markers, which constitute a set of bi-directional primers in combination with a restriction enzyme. This allows for the detection of specific SNPs linked to the trait. Bi-directional means that the orientation of the primers is such that one functions as the forward and one as the reverse primer in an amplification reaction of nucleic acid.

Alternatively, the step of detecting a molecular marker (step b) may in another preferred embodiment, comprise the use of a nucleic acid probe having a base sequence which is substantially complementary to the nucleic acid sequence defining said molecular marker (e.g. said SNP) and which nucleic acid probe specifically hybridizes under stringent conditions with a nucleic acid sequence defining said molecular marker. A suitable nucleic acid probe may for instance be a single strand oligonucleotide of the amplification product corresponding to the marker.

The step of detecting a molecular marker (step b) may also comprise the performance of a unique nucleic acid amplification reaction on said genomic DNA to detect said gene. This can suitable be done by performing a PCR reaction using a pair of marker-specific primers based on the internal or adjacent (up to 500 kilo base) sequence. In a preferred embodiment, said step b) comprises the use of at least one pair of primers defining a marker for said gene (e.g. being complementary to said marker or hybridizing specifically to said marker or allowing polymerase chain extension to occur when bound to said marker), or a pair of primers which specifically hybridize under stringent conditions with the nucleic acid sequence of a marker for said gene.

The step of detecting an amplified DNA fragment having a certain predicted length or a certain predicted nucleic acid sequence may be performed such that the amplified DNA fragment has a length that corresponds (plus or minus a few bases, e.g. a length of one, two or three bases more or less) to the expected length as based on the nucleotide sequence of the genes and markers identified herein. The skilled person is aware that markers that are absent in plants having the introgression as defined herein (donor plans), while they are present in the plants receiving the introgression (recipient plants) (so-called trans-markers), may also be useful in assays for detecting the introgression among offspring plants, although detecting the presence of a specific introgression is not optimally demonstrated by the absence of a marker.

The step of detecting an amplified DNA fragment having the predicted length or the predicted nucleic acid sequence may be performed by standard gel-electrophoresis techniques, real time PCR, or by using DNA sequencers. The methods need not be described here as they are well known to the skilled person. It should be noted that a marker is usually defined based on its nucleotide sequences in combination with its position relative to other markers on a linkage map.

Molecular Markers and Genes

Molecular markers are used for the visualisation of differences in nucleic acid sequences. This visualisation is possible due to DNA-DNA hybridisation techniques after digestion with a restriction enzyme (RFLP) and/or due to techniques using the polymerase chain reaction (e.g. STS, microsatellites, AFLP). All differences between two parental genotypes will segregate in a mapping population (e.g., $BC_1$, $F_2$) based on the cross of these parental genotypes. The segregation of the different markers may be compared and recombination frequencies can be calculated. The recombination frequencies of molecular markers on different chromosomes is generally 50%. Between molecular markers located on the same chromosome the recombination frequency depends on the distance between the markers. A low recombination frequency corresponds to a short genetic distance between markers on a chromosome. Comparing all recombination frequencies will result in the most logical order of the molecular markers on the chromosomes. This most logical order can be depicted in a linkage map. A group of adjacent or contiguous markers on the linkage map that is associated with spi^2, pinpoints the position of a gene associated with spi^2.

The markers identified herein may be used in various aspects of the invention as will now be illustrated. Aspects of the invention are not limited to the use of the markers identified herein. It is stressed that the aspects may also make use of markers not explicitly disclosed herein or even yet to be identified.

In the present invention amplified fragment length polymorphism (AFLP) markers, single nucleotide polymorphisms (SNPs), and insertion deletions (INDELs), microsatellite markers, restriction fragment length polymorphism (RFLP) markers, sequence-characterized amplified region (SCAR) markers, cleaved amplified polymorphic sequence (CAPS) markers or isozyme markers or combinations of these markers might be used. In general, a gene may span a region of several hundreds to thousands of bases. Although the sequence of the spi^2 gene has not yet been elucidated, the plants that have the genetic potential for exhibiting a particular phenotypic trait (spi^2) may be traced amongst a population of offspring plants through the observed correlation between the presence of a (string of contiguous) genomic marker(s) and the presence of the phenotypic trait. By providing a non-limiting list of markers, the present invention thus provides for the effective utility of the genes in a breeding program.

It is further important to note that the contiguous genomic markers can also be used to indicate the presence of the gene (and thus of the phenotype) in an individual plant, i.e. they can be used in marker assisted selection (MAS) procedures. In principle, the number of potentially useful markers is limited but may be very large, and the skilled person may easily identify additional markers to those mentioned in the present application. Any marker that is linked to the gene, e.g. falling within the physical boundaries of the genomic region spanned by the markers having established Lod scores above a certain threshold thereby indicating that no or very little recombination between the marker and the gene occurs in crosses; as well as any marker in linkage disequilibrium to the gene; as well as markers that represent the actual causal mutations within the gene, may be used in MAS procedures.

A Lod score ("logarithmic odds") is a measure of the likelihood of two loci being within a measurable distance of each other.

This means that the markers identified herein, are mere examples of markers suitable for use in MAS procedures. Moreover, when the gene, or the specific trait-conferring part thereof, is introgressed into another genetic background (i.e. into the genome of another plant line), then some markers may no longer be found in the offspring although the trait is present therein, indicating that such markers are outside the genomic region that represents the specific trait-conferring part of the gene in the original parent line only and that the new genetic background has a different genomic organisation. Such markers of which the absence indicates the successful introduction of the genetic element in the offspring are called "trans markers" and may be equally suitable in MAS procedures under the present invention.

Upon the identification of the gene, the gene effect (spi^2) is confirmed by determining the sympodial index of progenies respectively recombinant or segregating for the genes under investigation. Preferably, detecting the presence of a gene of the invention is performed with at least one of the markers for a gene as defined herein. The present invention therefore also relates to a method for detecting the presence of a gene for spi^2 as defined herein in tomato by the use of the said markers.

The nucleotide sequence of the genes of the present invention may be resolved by determining the nucleotide sequence of one or more markers associated with said gene and designing internal primers for said marker sequences that may then be used to further determine the sequence the gene adjacent to said marker sequences. For instance the nucleotide sequence of CAPS markers may be obtained by isolating said markers from the electrophoresis gel used in the determination of the presence of said markers in the genome of a subject plant, and determining the nucleotide sequence of said markers by for instance Sanger or pyro sequencing methods, well known in the art.

In embodiments of methods for detecting the presence of a gene in a tomato plant, the method may also comprise the steps of providing an oligonucleotide or polynucleotide capable of hybridizing under stringent hybridization conditions to a nucleic acid sequence of a marker linked to said gene, contacting said oligonucleotide or polynucleotide with nucleic acid of a tomato plant, and determining the presence of specific hybridization of said oligonucleotide or polynucleotide to said nucleic acid.

Preferably said method is performed on a nucleic acid sample obtained (isolated) from said tomato plant, although in situ hybridization methods may also be employed. Alternatively, and in a more preferred embodiment, the skilled person may, once the nucleotide sequence of the gene has been determined, design specific hybridization probes or oligonucleotides capable of hybridizing under stringent hybridization conditions to the nucleic acid sequence of said gene and may use such hybridization probes in methods for detecting the presence of a gene of the invention in a tomato plant.

Production of Tomato Plants Exhibiting Spi^2 by Transgenic Methods

According to another aspect of the present invention, a nucleic acid (preferably DNA) sequence comprising one or more of the genes as defined herein may be used for the production of a tomato plant exhibiting spi^2. In this aspect, the invention provides for the use of genes as defined herein or spi^2-conferring parts thereof, for producing a spi^2 tomato plant as defined herein, which use involves the introduction of a nucleic acid sequence comprising said gene in a suitable recipient plant. As stated, said nucleic acid sequence may be derived from a suitable donor plant. A suitable source according to the present invention for the spi^2 genes is tomato line *S. pennellii* LA716 (PI 246502 available from the Agricultural Research Service (ARS-GRIN) of the US Department of Agriculture, Washington D.C., USA).

The nucleic acid sequence that comprises a gene for spi^2, or a spi^2-conferring part thereof, may be transferred to a suitable recipient plant by any method available. For instance, the said nucleic acid sequence may be transferred by crossing a plant of line PI 246502 with a selected breeding line which is spi^3 or of which the spi is to be improved, i.e. by introgression, by transformation, by protoplast fusion, by a doubled haploid technique or by embryo rescue or by any other nucleic acid transfer system, optionally followed by selection of offspring plants comprising the spi^2 gene (as assessed by markers) and/or exhibiting spi^2. For transgenic methods of transfer a nucleic acid sequence comprising a gene for spi^2 may be isolated from said donor plant by using methods known in the art and the thus isolated nucleic acid sequence may be transferred to the recipient plant by transgenic methods, for instance by means of a vector, in a gamete, or in any other suitable transfer element, such as a bombardment with a particle coated with said nucleic acid sequence.

Plant transformation generally involves the construction of a vector with an expression cassette that will function in plant cells. In the present invention, such a vector consists of a nucleic acid sequence that comprises a gene for spi^2, which vector may comprise a spi^2 gene that is under control of or operably linked to a regulatory element, such as a promoter. The expression vector may contain one or more such operably linked gene/regulatory element combinations, provided that at least one of the genes contained in the combinations confers spi^2. The vector(s) may be in the form of a plasmid, and can be used, alone or in combination with other plasmids, to provide transgenic plants that exhibit spi^2, using transformation methods known in the art, such as the *Agrobacterium* transformation system.

Expression vectors can include at least one marker gene, operably linked to a regulatory element (such as a promoter) that allows transformed cells containing the marker to be either recovered by negative selection (by inhibiting the growth of cells that do not contain the selectable marker gene), or by positive selection (by screening for the product encoded by the marker gene). Many commonly used selectable marker genes for plant transformation are known in the art, and include, for example, genes that code for enzymes that metabolically detoxify a selective chemical agent which may be an antibiotic or a herbicide, or genes that encode an altered target which is insensitive to the inhibitor. Several positive selection methods are known in the art, such as mannose selection. Alternatively, marker-less transformation can be used to obtain plants without mentioned marker genes, the techniques for which are known in the art.

One method for introducing an expression vector into a plant is based on the natural transformation system of *Agrobacterium* (See e.g. Horsch et al., 1985). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of the plant. Methods of introducing expression vectors into plant tissue include the direct infection or co-cultivation of plant cells with *Agrobacterium tumefaciens*. Descriptions of *Agrobacterium* vectors systems and methods for *Agrobacterium*-mediated gene transfer are provided in U.S. Pat. No. 5,591,616. General descriptions of plant expression vectors and reporter genes and transformation protocols and descriptions of *Agrobacterium* vector systems and methods for *Agrobacterium*-mediated gene transfer can be found in Gruber and Crosby, 1993. General methods of culturing plant tissues are provided for example by Miki et al., 1993 and by Phillips, et al., 1988. A proper reference handbook for molecular cloning techniques and suitable expression vectors is Sambrook and Russell, 2001.

Another method for introducing an expression vector into a plant is based on microprojectile-mediated transformation (particle bombardment) wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes. Another method for introducing DNA to plants is via the sonication of target cells. Alternatively, liposome or spheroplast fusion has been used to introduce expression vectors into plants. Direct uptake of DNA into protoplasts using Ca $Cl_2$ precipitation, polyvinyl alcohol or poly-L-ornithine has also been reported. Electroporation of protoplasts and whole cells and tissues has also been described.

Other well known techniques such as the use of BACs, wherein parts of the tomato genome are introduced into bacterial artificial chromosomes (BACs), i.e. vectors used to clone DNA fragments (100- to 300-kb insert size; average, 150 kb) in *Escherichia coli* cells, based on naturally occurring F-factor plasmid found in the bacterium *E. coli* may for instance be employed in combination with the BIBAC system to produce transgenic plants.

Following transformation of tomato target tissues, expression of the above described selectable marker genes allows for preferential selection of transformed cells, tissues and/or plants, using regeneration and selection methods now well known in the art.

Production of Tomato Plants Exhibiting Spi^2 by Non-transgenic Methods

In an alternative embodiment for producing a tomato plant exhibiting spi^2, protoplast fusion can be used for the transfer of nucleic acids from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell, that may even be obtained with plant species that cannot be interbred in nature, is tissue cultured into a hybrid plant exhibiting the desirable combination of traits. More specifically, a first protoplast can be obtained from a tomato plant of accession PI 246502. A second protoplast can be obtained from a second tomato plant variety, preferably a tomato line that comprises commercially valuable characteristics, such as, but not limited to disease resistance, insect resistance, valuable fruit characteristics, etc. The protoplasts are then fused using traditional protoplast fusion procedures, which are known in the art.

Alternatively, embryo rescue may be employed in the transfer of a nucleic acid comprising the gene as described herein from a donor plant to a recipient plant. Embryo rescue can be used as a procedure to isolate embryo's from crosses wherein plants fail to produce viable seed. In this process, the fertilized ovary or immature seed of a plant is tissue cultured to create new plants.

The present invention also relates to a method for improving the spi^2 of a plant of a tomato breeding line, comprising the steps of:

a) crossing a plant of a tomato breeding line with a plant of tomato line PI 246502 or an offspring plant thereof harbouring the gene for spi^2 as described herein;

b) selecting a progeny tomato plant resulting from said crossing having an introgression from tomato accession PI 246502 or an offspring plant thereof associated with spi^2;

c) selfing and/or backcrossing said progeny tomato plant selected in step (b) using said tomato breeding line as a recurrent parent;

d) selecting a progeny tomato plant resulting from the selfing or backcrossing in step (c) having an introgression from tomato accession PI 246502 or an offspring plant thereof associated with spi^2, e) repeating said steps of selfing and/or backcrossing and selection of steps (c) and (d) to provide a plant of a tomato breeding line essentially homozygous for said introgression, wherein preferably at least one selection as performed in steps (b) or (d) is performed by marker-assisted selection.

In a preferred embodiment of such a method, said tomato breeding line is an elite line.

In an alternative preferred embodiment of the above method, the marker-assisted selection procedure comprises the selection for at least one marker as exemplified in the Examples below.

The introgression of the nucleic acid sequence comprising the spi^2 gene as described herein may suitably be accomplished by using traditional breeding techniques. The gene is preferably introgressed into commercial tomato varieties by using marker-assisted selection (MAS) or marker-assisted breeding (MAB). MAS and MAB involves the use of one or more of the molecular markers for the identification and selection of those offspring plants that contain one or more of the genes that encode for the desired trait. In the present instance, such identification and selection is based on selection of the gene of the present invention or markers associated therewith. MAS can also be used to develop near-isogenic lines (NIL) harboring the gene of interest, or the generation of gene isogenic recombinants (QIRs), allowing a more detailed study of each gene effect and is also an effective method for development of backcross inbred line (BIL) populations. Tomato plants developed according to this embodiment can advantageously derive a majority of their traits from the recipient plant, and derive spiˆ2 from the donor plant.

Crossing can be achieved by mechanically pollinating the female flower of one parent plant with pollen obtained from male flowers of another parent plant.

As discussed briefly above, traditional breeding techniques can be used to introgress a nucleic acid sequence encoding a gene for spiˆ2 into a recipient tomato plant requiring spiˆ2. In one method, which is referred to as pedigree breeding, a donor tomato plant that exhibits spiˆ2 and comprising a nucleic acid sequence encoding for the gene associated with spiˆ2 as defined herein is crossed with a recipient tomato plant (preferably a plant of an elite line) that exhibits agronomically desirable characteristics, such as, but not limited to, disease (e.g. TMV) resistance, insect resistance, valuable fruit characteristics, etc., but which is spiˆ3, or which requires improvement of spi towards spiˆ2. The resulting plant population (representing the $F_1$ hybrids) is then self-pollinated and set seeds ($F_2$ seeds). The $F_2$ plants grown from the $F_2$ seeds are then screened for spiˆ2. The population can be screened in a number of different ways.

First, the population can be screened using a visual inspection of the number of sympodia. Second, marker-assisted selection can be performed using one or more of the hereinbefore-described molecular markers to identify those progeny that comprise a nucleic acid sequence encoding for spiˆ2 as defined herein. Other methods, described above by methods for detecting the presence of a gene may be used. Also, marker-assisted selection can be used to confirm the results obtained from the spiˆ2 phenotype scores, and therefore, several methods may also be used in combination.

Inbred tomato plant lines exhibiting spiˆ2 can be developed using the techniques of recurrent selection and backcrossing, selfing and/or dihaploids or any other technique used to make parental lines. In a method of recurrent selection and backcrossing, the spiˆ2-conferring genetic element as disclosed herein can be introgressed into a target recipient plant (the recurrent parent) by crossing the recurrent parent with a first donor plant, which differs from the recurrent parent and is referred to herein as the "non-recurrent parent". The recurrent parent is a plant of which the spi is to be improved and possesses agronomically desirable characteristics, such as, but not limited to disease resistance, insect resistance, valuable fruit characteristics, etc. The non-recurrent, or donor, parent may suitably be a plant of line PI 246502 which comprises a nucleic acid sequence that encodes for spiˆ2. Alternatively, the donor parent can be any plant variety or inbred line that is cross-fertile with the recurrent parent and has acquired the gene for spiˆ2 in an earlier cross with a plant of line PI 246502, or a different accession having this trait. The progeny resulting from a cross between the recurrent parent and non-recurrent parent is backcrossed to the recurrent parent. The resulting plant population is then screened for the desired characteristics, which screening may occur in a number of different ways. For instance, the population can be screened using phenotypic screens as described herein.

As an alternative to phenotypic assays, marker-assisted selection (MAS) can be performed using one or more of the hereinbefore described molecular markers, hybridization probes or polynucleotides to identify progeny that comprise a nucleic acid sequence encoding the gene responsible for spiˆ2.

Following screening, the $F_1$ hybrid plants that exhibit a spiˆ2 phenotype or, more preferably, genotype and thus comprise the requisite nucleic acid sequence encoding for spiˆ2 are then selected and backcrossed to the recurrent parent for a number of generations in order to allow for the tomato plant to become increasingly elite. This process can be performed for two to five or more generations. In principle the progeny resulting from the process of crossing the recurrent parent with the non-recurrent parent are heterozygous for one or more genes that encode for spiˆ2.

In a preferred embodiment, a method of introducing a desired trait into a hybrid tomato variety comprises the steps of:

(a) crossing an inbred tomato parent with another tomato plant that comprises one or more desired traits, to produce F1 progeny plants, wherein the desired trait is spiˆ2 as conferred by the gene from PI 246502, or an offspring plant thereof;

(b) selecting said F1 progeny plants that have the desired trait to produce selected F1 progeny plants, preferably using molecular markers as defined herein;

(c) backcrossing the selected progeny plants with said inbred tomato parent plant to produce backcross progeny plants;

(d) selecting for backcross progeny plants that have the desired trait and morphological and physiological characteristics of said inbred tomato parent plant, wherein said selection preferably comprises the isolation of genomic DNA and testing said DNA for the presence of at least one molecular marker for the gene as defined above;

(e) repeating steps (c) and (d) two or more times in succession to produce selected third or higher backcross progeny plants;

(f) optionally selfing selected backcross progeny in order to identify homozygous plants;

(g) crossing at least one of said backcross progeny and/or selfed plants with another inbred tomato parent plant to generate a hybrid tomato variety with the desired trait and all of the morphological and physiological characteristics of hybrid tomato variety when grown in the same environmental conditions.

As indicated, the last backcross generation may be selfed in order to provide for homozygous pure breeding (inbred) progeny exhibiting spiˆ2. Thus, the result of recurrent selection, backcrossing and selfing is the generation of lines that are genetically homozygous for the genes associated with spiˆ2 as well as other genes associated with traits of commercial interest.

It should be noted that heterozygous plants having the gene for spiˆ2 may also be of interest as intermediate products, and such plants are therefore also an aspect of the present invention.

Tomato Plants and Seeds

The goal of plant breeding is to combine various desirable traits in a single variety or hybrid. For commercial crops, these traits may include resistance to diseases and insects, tolerance to heat and drought, reducing the time to crop maturity, greater yield, and better agronomic quality. Uniformity of plant characteristics such as germination, growth rate, maturity, and plant height may also be of importance.

Commercial crops are bred through techniques that take advantage of the plant's method of pollination. A plant is self-pollinated if pollen from one flower is transferred to the same or another flower of the same plant. A plant is sibling mated when individuals within the same family or line are used for pollination. A plant is cross-pollinated if the pollen comes from a flower on a different plant from a different family or line.

Plants that have been self-pollinated and selected for type for many generations become homozygous at almost all gene loci and produce a uniform population of true-bred progeny. A cross between two different homozygous lines produces a uniform population of hybrid plants that may be heterozygous for many gene loci. A cross of two plants each heterozygous at a number of gene loci will produce a population of heterogeneous plants that differ genetically and will not be uniform.

The development of a hybrid tomato variety in a tomato plant breeding program involves three steps: (1) the selection of plants from various germplasm pools for initial breeding crosses; (2) the selfing of the selected plants from the breeding crosses for several generations to produce a series of inbred lines, which, individually breed true and are highly uniform; and (3) crossing a selected inbred line with an unrelated inbred line to produce the hybrid progeny (F1). After a sufficient amount of inbreeding successive filial generations will merely serve to increase seed of the developed inbred. Preferably, an inbred line should comprise homozygous alleles at about 80% or more of its loci.

An important consequence of the homozygosity and homogeneity of the inbred lines is that the hybrid created by crossing a defined pair of inbreds will always be the same. Once the inbreds that create a superior hybrid have been identified, a continual supply of the hybrid seed can be produced using these inbred parents and the hybrid tomato plants can then be generated from this hybrid seed supply.

Using the methods as described above, the skilled person will be able to produce the required inbred lines and from those produce the commercial (F1) hybrid seeds by crossing said inbred lines.

The present invention will now be explained in more detail by way of the following non-limiting Examples.

EXAMPLES

Yield and Spi^2

In indeterminate tomato plants (protected tomato crops) the number of leaves between trusses is on average 3. The trait is called sympodial index (spi), and *Solanum lycopersicum* has spi=3. Fruit yield in tomato crops in the greenhouse is determined by the number of fruits per m2 and their weight. The number of fruits per m2 is determined by the number of fruits per truss and the number of trusses. It is expected that the yield can be increased in indeterminate tomato plants by increasing the number of trusses per $m^2$, and reducing the total number of leaves. An experiment was performed wherein the yield was measured (as total fruit weight and as number of fruits), comparing plants of a *S. lycopersicum* breeding line having spi^3 with a plant according to the present invention comprising the introgression from *S. pennellii* LA716 conferring spi^2 as described herein. It was demonstrated that the yield was increased significantly, indicated by a higher number of fruits and total yield for spi^2 plants (see Table 1).

TABLE 1

|  | total weight of fruits (in grams) | number of fruits |
|---|---|---|
| spi^3 common | 948 | 11 |
| spi^2 less leaves | 1626 | 22 |

Spi^2 Source.

*Solanum* Pennellii (formerly *Lycopersicum pennellii*) and other green fruited show spi^2, unlike the greenhouse tomato which has spi^3 (Rick, 1986 Report of the Tomato Genetics Cooperative (TGC)). The Tomato Genetics Resource Center (TGRC) stocklists includes the *S. pennellii* LA716 as spi^2. Damiaux (1985) described tomato lines with spi^2 using *S. Peruvianum* (formerly *L. peruvianum*). *S. pennellii* LA716 was back crossed to a *S. lycopersicum* line. During backcrossing, selection for the spi^2 trait was difficult due to the fact that the spi was very variable.

Spi Marker.

Carmel-Goren et al. (Plant Molecular Biology Plant Sciences 52(6):1215-1222 (2003)) published the sequences of the self-pruning gene family. We used the available sequences for sequencing LA 716, and developed CAPS markers based on the SNP differences, herein referred to as a spi-markers.

One such marker to select for spi consisted of a forward primer (5'-CAAGGGTTGAAGTTGGAGGA-3': SEQ ID NO:16) and a reverse primer (5'-GACGGTCAGCGTAC-CAGAAT-3'; SEQ ID NO:17) in combination with a restriction enzyme EcoR V (GAT|ATC). It results in a banding pattern (scores) for Spi^3 of two bands (289bp +452bp) and for spi^2 of one band (742bp). (See FIG. 5). The marker sequence is indicated in more detail in FIG. 7. The marker scores are:

Score 1=289 +452
Score 2=289 +452 +742
Score 3=742

In two segregating populations, we determined that the SP3D gene (AY186735, 6819 bp) was fully linked with the spi variation (See FIG. 5). Plants with SP3D homozygous for the donor LA716, gave on average 2.1 leaves between clusters. Heterozygous plants or plants homozygous for the *S. Lycopersicum*, gave higher number of leaves between clusters (see Table 1). The spi^2 trait shows to be more stable with a coefficient of variation of 5% than the spi^3 with 15%. The linkage between the marker and the trait was 100% in the 106 plants shown in table 2.

TABLE 2

| genotype* | average number of leaves between trusses | coefficient of variation in % |
|---|---|---|
| SLSL | 2.9 | 15% |
| SLSP | 2.3 | 8% |
| SPSP | 2.1 | 5% |

*SL *S. lycopersicum* (spi^3), SP *S. pennellii* (spi^2)

Spi Linkage Drag: Yellow Fruit Color.

During back crossing the spi marker was used. We found that the trait was linked to yellow fruit color (see table). Homozygous for the *S. pennellii* allele spi^2 is combined with yellow fruits. We found in the segregating population 2 plants that combined spi^2 with red fruit color. However, red fruit color is dominant over yellow, resulting in heterozygous plants with red fruits, and resulting in the next generation segregation for fruit color. The gene for yellow fruit color phytoene synthase (PSY-1 GenBank Accession X60441, from *L. esculentum* GTom5) is linked to SP3D in *S. pennellii*. We developed a marker based on the sequence differences, based on specific restriction endonuclease digestion of DNA of the plant or a part thereof.

One such marker to select for red color consisted of a forward primer (5'-GAGGTGGTG-GAAAGCAAACTAATA-3'; SEQ ID NO:18) and a reverse primer (5'-CTAAGGCTGCCGGGGTAATA-3'; SEQ ID NO:19) in combination with the restriction enzyme Bsh 1236 I (CGCG). It results in a banding pattern (scores) for red color of two bands (463 +482bp), for heterozygous genotype of three bands (463 bp +482bp +945bp) and for yellow color of one band (945 bp). (See FIG. 6), or, when bp countings are based on the PSY-1sequence of GenBank accession EF157835, marker scores are for red color (460 +474bp), for heterozygous genotype (460 bp +474bp +934bp) and for yellow color (934 bp). The marker sequence is indicated in more detail in FIG. 8.

TABLE 3

| | Number of plants | |
|---|---|---|
| genotype* | Red fruit | Yellow fruit |
| SLSL | 24 | 0 |
| SLSP | 65 | 1 |
| SPSP | 2 | 22 |

*SL *S. lycopersicum* (spiˆ3) SP *S. pennelili* (spiˆ2)

Spiˆ2—Red Fruit Color Recombinant.

To combine spiˆ2 and red fruit color using visual evaluation was not successful. The spi trait was too variable to select for, and we could not distinguish homozygous red fruit color from heterozygous red. Therefore, we used the spi marker and the color marker to select for recombinants that combined spiˆ2 and red fruit color. Table shows that plant 19, 20, 25 and 26 are homozygous for both spiˆ2 and red color, based on marker and visual data. Sequences of one recombinant plant are shown below.

TABLE 4

| Spi genotype | spi phenotype | Fruit color |
|---|---|---|
| SPSP | 2.1 | yellow |
| SPSP | 2.2 | yellow |
| SPSP | 2.1 | yellow |
| SPSP | 2.2 | yellow |
| SPSP | 1.8 | yellow |
| SPSP | 2.2 | yellow |
| SLSP | 2.2 | red |
| SLSP | 2.4 | red |
| SLSP | 2.3 | red |
| SLSP | 2.3 | red |
| SLSP | 2.2 | red |
| SLSP | 2.2 | red |
| SLSP | 2.2 | red |
| SLSP | 2.2 | red |
| SLSP | 2.4 | red |
| SLSP | 2.2 | red |
| SLSP | 2.3 | red |
| SLSP | 2.2 | red |
| SLSP | 2.2 | red |
| SLSP | 2.6 | red |
| SLSP | 2.2 | red |
| SLSP | 2.2 | red |
| SLSP | 2.3 | red |
| SLSP | 2.4 | red |
| SLSP | 2.3 | red |
| SLSP | 2.3 | red |

TABLE 4-continued

| Spi genotype | spi phenotype | Fruit color |
|---|---|---|
| SLSP | 2.4 | red |
| SLSP | 2.2 | red |
| SLSP | 2.2 | red |
| SLSP | 2.8 | red |
| SLSP | 2.2 | red |
| SLSP | 2.2 | red |
| SLSP | 2.5 | red |
| SLSP | 2.2 | red |
| SLSP | 2.4 | red |
| SLSP | 2.2 | red |
| SLSP | 2.2 | red |
| SLSP | 2.3 | red |
| SLSP | 2.2 | red |
| SLSP | 2.2 | red |
| SLSL | 2.8 | red |
| SLSL | 2.5 | red |
| SLSL | 2.5 | red |
| SLSL | 2.5 | red |
| SLSL | 3.7 | red |
| SLSP | 2.0 | red |
| SLSL | 2.5 | red |
| SLSL | 3.0 | red |
| SLSL | 3.0 | red |
| SLSL | 2.5 | red |
| SPSP | 2.1 | yellow |
| SPSP | 2.0 | yellow |
| SPSP | 2.2 | yellow |
| SPSP | 2.1 | yellow |
| SPSP | 2.1 | yellow |
| SPSP | 2.1 | yellow |
| SPSP | 2.1 | yellow |
| SPSP | 1.9 | yellow |
| SPSP | 2.0 | yellow |
| SPSP | 2.1 | yellow |
| SPSP | 2.0 | yellow |
| SPSP | 2.1 | red |
| SPSP | 2.1 | red |
| SLSP | 2.7 | red |
| SLSP | 2.3 | red |
| SLSP | 2.3 | red |
| SLSP | 2.5 | red |
| SLSP | 2.3 | red |
| SLSP | 3.0 | red |
| SLSP | 2.1 | red |
| SLSP | 2.4 | red |
| SLSP | 2.7 | red |
| SLSP | 2.7 | red |
| SLSP | 2.2 | red |
| SLSP | 2.3 | red |
| SLSP | 2.2 | red |
| SLSP | 2.6 | red |
| SLSP | 2.5 | red |
| SLSP | 2.3 | red |
| SLSP | 2.3 | red |
| SLSP | 2.3 | red |
| SLSP | 2.4 | red |
| SLSP | 2.1 | yellow |
| SLSP | 2.3 | red |
| SLSP | 2.3 | red |
| SLSP | 2.2 | red |
| SLSL | 3.5 | red |
| SLSL | 3.0 | red |
| SLSL | 3.0 | red |
| SLSL | 2.8 | red |
| SLSP | 2.3 | red |
| SLSL | 3.0 | red |
| SLSL | 2.8 | red |
| SLSP | 2.4 | red |
| SLSP | 2.7 | red |
| SLSP | 2.4 | red |
| SLSL | 2.7 | red |
| SLSL | 2.4 | red |
| SLSL | 3.0 | red |
| SLSL | 3.3 | red |
| SLSL | 3.0 | red |
| SLSL | 2.6 | red |
| SLSL | 4.3 | red |

TABLE 4-continued

| Spi genotype | spi phenotype | Fruit color |
|---|---|---|
| SLSL | 3.0 | red |
| SLSL | 3.0 | red |

TABLE 5

| Plant nr. | Spi | Fruit color | spi marker | color marker |
|---|---|---|---|---|
| 1 | 2.4 | Red | — | red? |
| 2 | 2.8 | Red | SLSP | red |
| 3 | 2.2 | Red | — | — |
| 4 | 2.4 | Red | SLSP | red? |
| 5 | 2.3 | Red | — | — |
| 6 | 2.0 | ND | — | — |
| 7 | 2.2 | Red | SLSP | red |
| 8 | 2.2 | Red | — | — |
| 9 | 2.2 | Red | — | — |
| 10 | 2.4 | ND | — | — |
| 11 | 2.0 | Yellow | SPSP | yellow |
| 12 | 2.0 | Yellow | SPSP | yellow |
| 13 | 2.0 | Yellow | SPSP | yellow |
| 14 | 2.0 | Yellow | SPSP | yellow |
| 15 | 2.4 | Red | SLSP | red |
| 16 | 2.2 | Red | SLSP | red |
| 17 | 2.0 | Red | | |
| 18 | 2.4 | Red | SLSP | red |
| 19 | 2.0 | Red | SPSP | red |
| 20 | 2.0 | Red | SPSP | red |
| 21 | 2.0 | Yellow | SPSP | — |
| 22 | | Yellow | — | — |
| 23 | 2.5 | Red | SLSP | red |
| 24 | 2.0 | Red | SLSP | red |
| 25 | 2.0 | Red | SPSP | red |
| 26 | 2.0 | Red | SPSP | red |
| 27 | 2.0 | Red | SLSP | red |
| 28 | 3.7 | Red | SLSP | red |
| 29 | 2.3 | Red | — | — |
| 30 | 2.4 | Red? | SLSP | red |
| 31 | 2.4 | Red | — | red |
| 32 | 2.0 | Red? | — | — |
| 33 | 2.2 | Red | SLSP | red |
| 34 | 2.2 | Red | SLSP | red |
| 35 | 2.1 | Red | SLSP | red |
| 36 | 2.0 | Red | SLSP | red |
| 37 | 3.0 | Red | SLSL | red |
| 38 | 2.8 | Red | SLSL | red |
| 39 | 2.0 | Red | — | — |
| 40 | 2.0 | Red | SLSP | red |

---

The invention claimed is:

1. A cultivated *Solanum lycopersicum* tomato plant having an average sympodial index of between 1.8 and 2.2 and having red-colored fruits with yellow skin, whereby said plant comprises a SP3D gene from the family of self-pruning genes of *Solanum pennellii*, and a phytoene synthase PSY 1 gene of *S. lycopersicum*.

2. The plant according to claim 1, wherein said plant is a recombinant plant comprising an introgression from a plant of a donor line of *S. pennellii* having an average sympodial index of between 1.8 and 2.2.

3. The plant according to claim 2, wherein said donor plant is a plant of the wild tomato species *S. pennellii* LA716.

4. The plant according to claim 1, wherein the total fruit weight per plant is above 1000 grams.

5. The plant according to claim 1, produced by a method comprising:
   a) crossing a recipient *Solanum lycopersicum* tomato plant capable of producing red-colored fruits, with a plant of a donor line of *S. pennellii* having an average sympodial index of between 1.8 and 2.2 and producing green tomatoes;
   b) collecting the seeds resulting from the cross in step (a),
   c) regenerating the seeds into plants;
   d) providing one or more backcross generations by crossing the plants of step (c) or selfed offspring thereof with one or more recipient of *S. lycopersicum* tomato plants to provide backcross plants;
   e) selfing plants of step (d) and growing the selfed seed into plants;
   f) optionally repeating said steps of backcrossing and selfing of steps (d) and (e); and g) identifying and selecting from the plants grown in step (c), (e) or (f) plants having an average sympodial index of between 1.8 and 2.2 and producing red-colored fruits, wherein the step of identifying and selecting a plant having an average sympodial index of between 1.8 and 2.2 is performed by marker-assisted selection comprising the use of a marker linked to a SP3D gene from the family of self-pruning genes of *S. pennellii*, and the step of identifying and selecting a plant producing red colored fruits comprises use of a marker linked to phytoene synthase PSY 1 of *S. lycopersicum*.

6. The plant according to claim 1, wherein said plant is indeterminate.

7. Fruit of the plant according to claim 1.

8. Seed of the plant according to claim 1, comprising a SP3D gene from the family of self-pruning genes of *S. pennellii*, and a phytoene synthase PSY 1 gene of *S. lycopersicum*.

9. The plant according to claim 5, wherein said donor plant is a plant of the wild tomato species *S. pennellii* LA716.

10. The plant according to claim 5, wherein the total fruit weight per plant is increased by at least 10% relative to a recipient-*Solanum lycopersicum* tomato plant lacking an introgression comprising the SP3D gene of *S. pennellii* LA716.

11. The plant according to claim 5, wherein the total fruit weight per plant is above 1300 grams.

12. A cultivated *Solanum lycopersicum* tomato plant having an average sympodial index of between 1.8 and 2.2 and producing red-colored fruits, said plant comprising an introgression comprising the SP3D gene of *S. pennellii*, and comprising the phytoene synthase PSY 1 gene of *S. lycopersicum*.

13. The *Solanum lycopersicum* plant according to claim 12, comprising an introgression comprising the SP3D gene of *S. pennellii* LA716.

14. The plant according to claim 1, wherein the presence of the SP3D gene from the family of self-pruning genes of *S. pennellii* and the phytoene synthase PSY1 gene of *S. lycopersicum* is determined by marker-assisted selection.

15. The plant according to claim 14, wherein [the marker linked to] the SP3D gene of *S. pennellii* is the sequence provided in SEQ ID NO:9.

16. The plant according to claim 14, wherein the marker linked to the SP3D gene of *S. pennellii* is the sequence provided in SEQ ID NO:14.

17. The plant according to claim 14, wherein said marker linked to the SP3D gene of *S. pennellii* consists of a primer having SEQ ID NO:16 and a primer having SEQ ID NO:17, in combination with an EcoR V restriction enzyme, whereby a banding pattern of one band of 742 bp is indicative of a plant having an average sympodial index of between 1.8 and 2.2.

18. The plant according to claim 14, wherein [the marker linked to] the phytoene synthase PSY1 gene of *S. lycopersicum* is SEQ ID NO:6.

19. The plant according to claim 14, wherein the marker linked to the phytoene synthase PSY 1 gene of *S. lycopersicum* is SEQ ID NO:11.

20. The plant according to claim 14, wherein said marker linked to the phytoene synthase PSY1 gene of *S. lycopersicum* consists of a primer having SEQ ID NO:18 and a primer having SEQ ID NO:19, in combination with a Bsh 1236 I restriction enzyme, whereby a banding pattern of two bands of 463 bp and 482 bp is indicative of a plant producing red colored fruits.

* * * * *

SEQUENCE LISTING

<160> NUMBER OF SEQ ID NOS: 19

<210> SEQ ID NO 1
<211> LENGTH: 177
<212> TYPE: PRT
<213> ORGANISM: Solanum lycopersicum

<400> SEQUENCE: 1

Met Pro Arg Glu Arg Asp Pro Leu Val Val Gly Arg Val Gly Asp
1               5                   10                  15

Val Leu Asp Pro Phe Thr Arg Thr Ile Gly Leu Arg Val Ile Tyr Arg
                20                  25                  30

Asp Arg Glu Val Asn Asn Gly Cys Glu Leu Arg Pro Ser Gln Val Ile
        35                  40                  45

Asn Gln Pro Arg Val Glu Val Gly Gly Asp Leu Arg Thr Phe Phe
50                  55                  60

Thr Leu Val Met Val Asp Pro Asp Ala Pro Ser Pro Ser Asp Pro Asn
65                  70                  75                  80

Leu Arg Glu Tyr Leu His Trp Leu Val Thr Asp Ile Pro Ala Thr Thr
                85                  90                  95

Gly Ser Ser Phe Gly Gln Glu Ile Val Ser Tyr Glu Ser Pro Arg Pro
            100                 105                 110

Ser Met Gly Ile His Arg Phe Val Phe Val Leu Phe Arg Gln Leu Gly
            115                 120                 125

Arg Gln Thr Val Tyr Ala Pro Gly Trp Arg Gln Asn Phe Asn Thr Arg
    130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Arg Arg Ser Ala
                165                 170                 175

Asp

<210> SEQ ID NO 2
<211> LENGTH: 6819
<212> TYPE: DNA
<213> ORGANISM: Solanum lycopersicum

<400> SEQUENCE: 2

| | | | | | |
|---|---|---|---|---|---|
| tacaatgtca | aaactaggaa | aaaattacta | gaggagaagg | taatttgtgt | cgatttcctt | 60 |
| aggagtcttc | actaaagaag | ttttcctcta | aggatccaaa | gtctcgtaga | ccgaggataa | 120 |
| aggctctatt | aacgctagag | cgattgaata | aacttgttgt | aacccatgga | tcaccctcta | 180 |
| ctaggactcg | taaaaaattc | agaggataca | caatacattt | aaattaattt | tcttaagcat | 240 |
| tcaacaatac | atttattttg | tttttgcatc | tttatatgac | gttactgatc | ttagagctag | 300 |
| ggctaaagtt | acaagcacta | tgaaaacatc | caaacttttg | actcttctac | tattaaacta | 360 |
| ctttatttca | ttctattcac | ttttgtcctt | gctaataaat | caaaccttta | gtaaacgaat | 420 |
| ataaaaagaa | ccaaacaaac | acatgtgctc | ttgtcctcct | acaaattcaa | cccaacctat | 480 |
| tttagggtaa | acaaattcgg | aaacatttcg | gatataactg | gtgaatttct | aacacctttc | 540 |
| gtaaagtaaa | atatatttat | tcaaactcat | aaatttaaaa | ttataaattc | gtgttaggaa | 600 |
| ggaatgctaa | gaaatagaat | gagtgaaaag | agttttaaag | aaggagagaa | ccaaagtcat | 660 |
| tatcagactg | aaatgtatgt | caaacagata | caatgtatgg | taatgataga | actaattaac | 720 |
| tacatgccac | taattgcact | atattatcag | ctacccacct | aactaacttc | tattaaatta | 780 |
| actgttaaac | caacaattta | acttactcct | cttttcatat | tactctgatc | tctattgatc | 840 |
| tagcatatca | ttttagaaaa | ctttaattat | atgtgtatat | taatctaatc | tcgttagcaa | 900 |
| tgtttaggaa | ctatgactat | tagtttaagt | tgttattcaa | tacttaaggt | agaaaaagaa | 960 |
| aaatatagca | aaattttctt | attttcataa | attaggttag | taagtaatta | ttttttagtat | 1020 |
| gaagataaaa | gtaatattaa | aggtgggagt | aactaatatg | taactatatg | tcatagtcaa | 1080 |
| caaatcagta | gcatggattt | ctaagactac | caacttaaag | aataaggtga | taatttaaac | 1140 |
| cagtttaggt | aggggtaagg | gtaaaatatt | ggaaaaatca | tttaaatata | taacttattt | 1200 |
| tattataatt | tttaaaattt | tctactattc | gaaaaaaaa | atataacaaa | tattacttta | 1260 |
| cgtgatgtat | cagtcggata | tatcacttta | cactatatat | cgctcagata | catcacttta | 1320 |
| tgcgatatat | cgcttgtata | caacacttta | cgcgttctat | ctggacgtat | gcgatgtatc | 1380 |
| gggatattgt | tactttacgt | gatgtatcgg | tcagatacac | tactttacgc | gatgtagaac | 1440 |
| gttgagagat | gttccagaat | caagacacga | tgatattggg | acgctttggg | gtgtattcga | 1500 |
| atttcaccaa | attatttttt | ttttgtaatt | tgaaaaaaag | tccgtttatt | cataacataa | 1560 |
| tgaaatttgt | gtaaaatcat | gaaaaatatt | ttaacacaaa | ttgctatgta | gaagtaattt | 1620 |
| ccacaaaaaa | aaaaaaaatt | ctaatccgca | gctgctaccc | tttggccttt | cctttgtcaa | 1680 |
| aaaaaataaa | atgaaaacta | atcttccaaat | atgtcatgat | tcgattagaa | gaattcctag | 1740 |
| aaaacctatg | gttgtaaggt | gggaaaagag | aagtaattaa | aaaaggcacg | taccagattc | 1800 |
| tttaggagga | tatgacagca | aaaggtgcta | ccatatgtgt | atatatatat | acacacacat | 1860 |
| tctacctcta | cacttgtaaa | aatatgcata | gcccgataag | aaactagcta | gctaggagta | 1920 |
| ctccttgtgtt | gtgttttagc | tcacaaatac | acaaaagtta | gccatagcta | gtttttattt | 1980 |
| tgtttatcgt | caaccatcgt | catgcctaga | gaacgtgatc | ctcttgttgt | tggtcgtgtg | 2040 |
| gtaggggatg | tattggaccc | tttcacaaga | actattggcc | taagagttat | atatagagat | 2100 |

```
agagaagtta ataatggatg cgagcttagg ccttcccaag ttattaacca gccaagggtt    2160
gaagttggag gagatgacct acgtacctttt ttcactttgg taatatttct tatatttttt    2220
gtttgggaat atagttaagt tgattttcat aagcaaagta aaaagtattt ttgtcttttt    2280
gtaaaggtta tggtggaccc tgatgctcca agtccgagtg atccaaatct gagagaatac    2340
cttcactggt ccgtattttt tccttattct ctcttctttt catctctttc ttttttgacc    2400 ttttttactta attatattct ttagtaataa tatatgatga tatcctttt  aaaaattgga    2460 aatacgaaaa ggagaaatga agaggagatt tacatgtgag ggagcagatg gtagaaatat    2520
ataaatgtga agatatatat tcttgaactt aaaaacaagc tactaaaata aaaatgaata    2580
aaatatttac tctgtcaata ttctgtacta tattggtcaa tgaatattta tattattcat    2640
gactttaaaa atagtcaaac gagacataac gtaaaagtca aaatacgttt aagctcattc    2700
atataaatga atatttttaa aatttgttgc atccatcaaa atatctactt tttaaggaat    2760
gatatttatt tcataatatt catatttgat tcgttgatgg atagatttta ttctttaaaa    2820
aattaaataa aaaaaataaa attggcctag tcatatccat ctaaaatggg tgagattctg    2880
gtacgctgac cgtcttataa ttcccaataa aaacttttgg agaaaaaagg gaacacaaaa    2940
aaatgaagta gtgcaccaat agaatcactt ctcacctcct tatagctagt acggattatt    3000
cccttcatgt gtgccacagt catgcacaat ccatattata atttccaaaa taattagttg    3060
ttcacgtttg aattgatcat aaatgatatt accatttatc ctttttactt attaagtaga    3120
tagattaaaa aatttaagat tttcaaaaag ttctacattt taaaaataa  tcaattgaag    3180 gtataaaaaa gttgtccttc cttaatttct caagatggat aagtaattaa gaacaactaa    3240
aaaaaagcga acaaataatt agagatcgaa tgaatatttta tcaatcctca tttcaccaag    3300
tcattaaatt attttatgac caaaatgttt actcattttg cttaaatatc aagaaaattg    3360
ttgaattatt tcttatagaa atatcactca acatcagtat ctaagtagta ctcatttcgt    3420
ttctatttat atatcatttt tattaaatat aaatgttttc ttgatatttta tttatttcac    3480 aaaatcaaaa tttgacttat gattactaaa taattaattt aatttaatta atcaaaataa    3540
attaatttat ctcttttgca aaagttaact ttaagagaac actaattaag aatataataa    3600
taaatttagt taatttttt  aaaagatata aaatctaaat tagtgacata taaatagaaa    3660
gaggggaaag tagtagttta actcttatgg tttgataagg tgtgtgctaa atgacaacat    3720 cttttcttgtc tcgtaaagtt aacatctttg taggtggtga gtaagtgagt gaatgccatt    3780
gaatgaagag attatttgtt tttgtcacct ttaccactaa agttttgtct attttttattc    3840 ttcgaattcc tccagtacaa gattttattt ttgatattcc tttctttgga attcagtgtt    3900
ggtataaata ggatctattt ggctatccac atatattttt aaataaaaat cagtatttag    3960
tcatttaaat tacatttcat ggattatact cgttaaaaaa aatatattta agcaattaaa    4020
tattatttgt tgaacatagg aaaaatgatt tgaaatatat tcaaactttg atcacaattg    4080
tgataacaat ttcaaatttt gggaaggacc ttttacccct tgcactattt atagtatatt    4140
ttaaatgtat atatatgtca acataaatat aataaatatt gcattattat atatagtaac    4200
ttgttcacgt ggatacatat atacctgtaa aatatactat taaataatat aggagatagt    4260
aggtcctgct caaagttaga gattgttata gcaatttcga tcaaagatat atttcaaact    4320 attttttccta aaagatataa ccaaatacaa ttttatctttt aatttcaata tttgcaaata    4380
aagtgaaaaa atatttatac caagtaggat gaattaaaaa ttagggtttt ttttcctctt    4440
gttatatata taactaatcg tcattttttt attaatgaat cgtcgacagg ttggtcaccg    4500
```

```
atattccagc taccacaggt tcaagttttg gtgagaatcc tcttttgtt aattgtttgt    4560 ttgttgtctt cccatgttta cattttttta aaaaaaaaac aaactaattt taaaggtaga    4620
attaaaaaaa aatcattatc gtatttaaaa atatattttt ataataatat ggacgaataa    4680
tatgaaacta acagagtaat gacaaaggaa tttatactga gcgggcaatg ttgcgttaaa    4740
tcatgtttgt cctaaacttt taaaacctag gaaagggaat gaaatctatt ctcaattaac    4800
gtgattaaat attctaaaca attgatatcc tttaattatg tcccacacta cgccaaaagt    4860
tcttaagcat tacactctaa aatttgtatg cataacatta aaagatcatt acctatttgg    4920
ctaaaatttt tacaataagt ttatttaaa aagtgttcct ttttttcccc tctcaaaaac    4980
acacttgtgt tactcttgat ttttctctca aaagtttagt taaatactta agtttttta    5040 aaataatttt tttatgaaaa aagaaaaaaa acattttgg ctaaccaaac aggtttagga    5100
gacttgcgct ctgccataag tatttcccca ttcactttc ttccatttt atttatgatt    5160 ttttttaaca tattaagaaa gctatttgtt tcatgctctt caataatttc ttattctcca    5220
aattaacata gatattgtgg taaaacacca taatagttat tgtatatttg tataccttt    5280 caaatatata tactctctaa taagatcaca agataaaaaa acatttattg gtgaataaat    5340
ttgacataac tttaatttaa ttataacaca aaattcaaaa gttttatttc tcaacttaaa    5400
aatttggtgt caagtcagaa gtagatgtga taattttgt ttttgaaatt ggagggagta    5460
tcttgttgaa aatattggat atgtacataa gaagtagtca tttgaaatgc attgaaactt    5520
gataaaaaca taagtagcta gctagtgcat gaaagtttgg ttgtttatgt acttttaata    5580
tgtagggcaa gaaatagtga gctatgaaag tccaagacca tcaatgggaa tacatcgatt    5640
tgtatttgta ttattcagac aattaggtcg gcaaacagtg tatgctccag gatggcgtca    5700
gaatttcaac acaagagatt ttgcagaact ttataatctt ggtttacctg ttgctgctgt    5760
ctattttaat tgtcaaagag agagtggcag tggtggacgt agaagatctg ctgattgatc    5820
aactccatct actacaaaaa acaaaaaaac aatgatattt ttagctaata ataaccacca    5880
atatctacta cttctcttac aactttagta gtatctatag ttatctttt taatctactc    5940 ttttacttct ttactatatt gtcttcctct caatttattt gaattagtga cttgatatca    6000
agtttcaata aagaaacaaa gactgacttt agaattttgt gatttacaat aagttgtaca    6060
tatttgtatg actatcttaa aaagttaaat cattattatt aaatataaaa atatgattaa    6120
tttaaaagga agtaaattat ataaaacgtt aatttttttt tatagtttag ctcttaaaaa    6180
aaaattataa caattaaaag tattgaatga agaagtttg taactagtct ctgttattcc    6240
tctataaaac agtatatttt cttgttactt ttataaattt ctaagatatg aacttgagta    6300
ttatttggca taaacaagt tccaataaag aatcttgagt ggaagtactt gtagggcagt    6360
aaaaaggccg cctctctgtc accaaacaag ttgagtttgc tttggaaata caacagtcgt    6420
catccaactt cctttccaa aaagccttaa cagtggatat taatgtacaa acttaccttc    6480
gttcaaacga cgtacataat cacatttaca ttgcatcgtg aaaaattata ttttcttcgt    6540
tcattttaaa tgtcatgatt tttattttta taaaaaattt taaataacat tttaatgttt    6600
atattttcat cgtatcgata tgcaaaaaat tacaagttat agagttttg tatatctatt    6660 ttttaaaata tcaaattaat aataattaat ttaactttga aaattaatgt aattgacttc    6720
cgaaaaatac aaatgacaaa taaaaatgaa aaagtaaata ataaaatctg attaaaacta    6780
tagtctaatt tatataaagg aaccctaaga atcttctaa                          6819
```

<210> SEQ ID NO 3
<211> LENGTH: 20
<212> TYPE: DNA
<213> ORGANISM: Artificial sequence
<220> FEATURE:
<223> OTHER INFORMATION: Primer sequence

<400> SEQUENCE: 3
caagggttga agttggagga                                                     20

<210> SEQ ID NO 4
<211> LENGTH: 20
<212> TYPE: DNA
<213> ORGANISM: Artificial sequence
<220> FEATURE:
<223> OTHER INFORMATION: Primer sequence

<400> SEQUENCE: 4
attctggtac gctgaccgtc                                                     20

<210> SEQ ID NO 5
<211> LENGTH: 412
<212> TYPE: PRT
<213> ORGANISM: Solanum lycopersicum

<400> SEQUENCE: 5

Met Ser Val Ala Leu Leu Trp Val Val Ser Pro Cys Asp Val Ser Asn
1               5                   10                  15

Gly Thr Ser Phe Met Glu Ser Val Arg Glu Gly Asn Arg Phe Phe Asp
            20                  25                  30

Ser Ser Arg His Arg Asn Leu Val Ser Asn Glu Arg Ile Asn Arg Gly
        35                  40                  45

Gly Gly Lys Gln Thr Asn Asn Gly Arg Lys Phe Ser Val Arg Ser Ala
    50                  55                  60

Ile Leu Ala Thr Pro Ser Gly Glu Arg Thr Met Thr Ser Glu Gln Met
65                  70                  75                  80

Val Tyr Asp Val Val Leu Arg Gln Ala Ala Leu Val Lys Arg Gln Leu
                85                  90                  95

Arg Ser Thr Asn Glu Leu Glu Val Lys Pro Asp Ile Pro Ile Pro Gly
            100                 105                 110

Asn Leu Gly Leu Leu Ser Glu Ala Tyr Asp Arg Cys Gly Glu Val Cys
        115                 120                 125

Ala Glu Tyr Ala Lys Thr Phe Asn Leu Gly Thr Met Leu Met Thr Pro
    130                 135                 140

Glu Arg Arg Arg Ala Ile Trp Ala Ile Tyr Val Trp Cys Arg Arg Thr
145                 150                 155                 160

Asp Glu Leu Val Asp Gly Pro Asn Ala Ser Tyr Ile Thr Pro Ala Ala
                165                 170                 175

Leu Asp Arg Trp Glu Asn Arg Leu Glu Asp Val Phe Asn Gly Arg Pro
            180                 185                 190

Phe Asp Met Leu Asp Gly Ala Leu Ser Asp Thr Val Ser Asn Phe Pro
        195                 200                 205

Val Asp Ile Gln Pro Phe Arg Asp Met Ile Glu Gly Met Arg Met Asp
    210                 215                 220

Leu Arg Lys Ser Arg Tyr Lys Asn Phe Asp Glu Leu Tyr Leu Tyr Cys
225                 230                 235                 240

Tyr Tyr Val Ala Gly Thr Val Gly Leu Met Ser Val Pro Ile Met Gly
                245                 250                 255

Ile Ala Pro Glu Ser Lys Ala Thr Thr Glu Ser Val Tyr Asn Ala Ala
            260                 265                 270

Leu Ala Leu Gly Ile Ala Asn Gln Leu Thr Asn Ile Leu Arg Asp Val
        275                 280                 285

Gly Glu Asp Ala Arg Arg Gly Arg Val Tyr Leu Pro Gln Asp Glu Leu
    290                 295                 300

Ala Gln Ala Gly Leu Ser Asp Glu Asp Ile Phe Ala Gly Arg Val Thr
305                 310                 315                 320

Asp Lys Trp Arg Ile Phe Met Lys Lys Gln Ile His Arg Ala Arg Lys
                325                 330                 335

Phe Phe Asp Glu Ala Glu Lys Gly Val Thr Glu Leu Ser Ser Ala Ser
            340                 345                 350

Arg Phe Pro Val Trp Ala Ser Leu Val Leu Tyr Arg Lys Ile Leu Asp
        355                 360                 365

Glu Ile Glu Ala Asn Asp Tyr Asn Asn Phe Thr Lys Arg Ala Tyr Val
    370                 375                 380

Ser Lys Ser Lys Lys Leu Ile Ala Leu Pro Ile Ala Tyr Ala Lys Ser
385                 390                 395                 400

Leu Val Pro Pro Thr Lys Thr Ala Ser Leu Gln Arg
                405                 410

<210> SEQ ID NO 6
<211> LENGTH: 4958
<212> TYPE: DNA
<213> ORGANISM: Solanum lycopersicum

<400> SEQUENCE: 6
tcttgatttc ttgaaacaaa ggtttgtttc ccttcacttc ttgatatgta aagttgcaat      60
ctttataact ttctattgct ttgctagtgt ttttgttata tacaggggt ggagttagag      120
ggtaagttac gcatttagtc gtaactttag tcaaacttcg taataattta gtaagttaaa     180
atatattaga aattttcaga attcataaac tttaaatttt aaattttgac ttcgctttgt     240
gtgactatac aattacagaa attcagagtg gccattgttg aaagagaggg tggaatttgt     300
gtaagttttg tttcctttca gttcttgata tataaagttg caatctttaa cattctttgt     360
tcactttcta taggtttgct aggttcggtt aaattcagta gctttagttt aaaccctatg     420
cggaatagag aatgtgtaaa ctttaaactt caaattttgg ctccgcatac gactagcgac     480
tatataataa taggaattga gcacttggct tttgtatata gcttctatgt gtaccaaaat     540
tagaaaatca ggcgattatt ataatcttgt tgactaaata tagaatgcat ccattacccc     600
caaaaagtgt gattccactg tcataggagg ttttttttat ttcattttat ttgtgctttc     660
aataatgtag agtagtttta caaagatcct tcctttgtga cacatggtag taatattgct     720
gattttgctg tagttttggg gttataaagt tcaaattatt tatctggagg gtaggggtg      780
ggggtgtcta taatgccagg ttatggtttt acgtgaacct caataaatta ttggtagaat     840
ctaagaaatc cactcagtgt tccgtgcggt ggtcttgctt ttgatttcag catcactggt     900
agttgattgt gtttagatta tcacattatt ctgtggctgt aactgtatcc ttgttagttg     960
ctttgttcct acactgttgt tttccctctt ttataccctat tttgatatgt tgtactcgaa    1020
cgagggtcat cggggaacaa cctctttacc tccgtgaggt agagctatgg tctgtgtcca    1080
ctctacccct cccagatccc tcttgtagga tttcactata ttgtaatatt aacttgaggt    1140
cactatagga gctcaaaaac ttctaatttt gaatcaatgt ctggttatac tttttttgtc    1200

-continued

```
ataactgtat ctcaaatgtg gtgtttggtt tatctcattt tgcagaagtc aagaaacagg      1260
ttactcctgt ttgagtgagg aaaagttggt ttgcctgtct gtggtctttt tataatcttt      1320
ttctacagaa gagaaagtgg gtaattttgt ttgagagtgg aaatattctc tagtgggaat      1380
ctactaggag taatttattt tctataaact aagtaaagtt tggaaggtga caaaaagaaa      1440
gacaaaaatc ttggaattgt tttagacaac caaggttttc ttgctcagaa tgtctgttgc      1500
cttgttatgg gttgtttctc cttgtgacgt ctcaaatggg acaagtttca tggaatcagt      1560
ccgggaggga aaccgttttt ttgattcatc gaggcatagg aatttggtgt ccaatgagag      1620
aatcaataga ggtggtggaa agcaaactaa taatggacgg aaattttctg tacggtctgc      1680
tattttggct actccatctg gagaacggac gatgacatcg gaacagatgg tctatgatgt      1740
ggttttgagg caggcagcct tggtgaagag gcaactgaga tctaccaatg agttagaagt      1800
gaagccggat atacctattc cggggaattt gggcttgttg agtgaagcat atgataggtg      1860
tggtgaagta tgtgcagagt atgcaaagac gtttaactta ggttagcttc ttcaatctat      1920
tcattcgttt accaaatatt atttggtaag cactaattat gaatatatat atgttcatgt      1980
tattgatgaa gacaaaattt gatctttgtt tgtttattca ggaactatgc taatgactcc      2040
cgagagaaga agggctatct gggcaatata tggtgaggtt tctagccatt taataacagt      2100
tacgcgcaca aacacatatg attaatcggg gacgagaaaa aagaaatga agtttgagtt      2160 ttgagggtca tatgtaatag gtaaatccga gcttgactag cttgagatgt ttattgtcat      2220
atcatgctca atactaacca aaacactgaa aaagaacttg attatattta catactaata      2280
ttttcatttg cgttgctgtt cacatttta cctatgaaac tggttttgt gatttgttat       2340 acttcatatt cgatgttaat aaaatatatc attcctccct ttttctccac ttcaagcttt      2400
actgtagtgt tgaaggggga aactccttt aatgattgca tatataaacg aacttcttga      2460
gttgaatagt ttctcattat gatctgttta aacagtatgg tgcagaagaa cagatgaact      2520
tgttgatggc ccaaacgcat catatattac cccggcagcc ttagataggt gggaaaatag      2580
gctagaagat gttttcaatg ggcggccatt tgacatgctc gatggtgctt tgtccgatac      2640
agtttctaac tttccagttg atattcaggt tagtctacca attctatggt ctttatattt      2700
gttcaatttg cgtttgatgt cactttttgct gagggctttt ctaatagctt acttcagcct      2760
agcggaaatg tttgtagttg aatctctagt tctgtctcct atatctgttt ctctcgtcct      2820
agatactaca catacttcat ttctgttta acattttatt cgtcttttgg tgttgttttg      2880
tatgtgaatc atatatttgg aacagaatca ttattagttc acatgatttc atttgctttc      2940
ttcaatagcg taattgtcta accttccaat atatgttgca gccattcaga gatatgattg      3000
aaggaatgcg tatggacttg agaaaatcga gatacaaaaa cttcgacgaa ctatacctt       3060 attgttatta tgttgctggt acggttgggt tgatgagtgt tccaattatg ggtatcgccc      3120
ctgaatcaaa ggcaacaaca gagagcgtat ataatgctgc tttggctctg gggatcgcaa      3180
atcaattaac taacatactc agagatgttg gagaagagta agtacaaagc tgtgttttac      3240
gcacataatt tttttgcta atatttacat atcaaaatat aggaaaatga gctcttcggt       3300
tatccggttt atatttttt tatgtcaaca taatagtata aagtaattag tatcagtcgt       3360
tctgggaata aaattgcaga actcaattta gccgtgttgt gaaatcctgc ttgttttgag      3420
agcttaaagc tcattagtta gtcgttagag acgaagaaat tcttcgttgt ccatctttat      3480
tccaccttaa agttgtgata ttttcattat tggtacattt ggcaaaaaca cctgaacaaa      3540
tttatgacgg atgcctttg aaagtcacta tacctgtcta gtcggcgttt atcacatttc       3600
```

```
tttgacatat tgaactttga aacatgatat cagctctaga cagtgacgag ccatgatcaa    3660
tttctttcct ttattctttc tttggaagtg ccgtatttag gcttccgttg ttcttatata    3720
ttgctttccc tgcagtgcca gaagaggaag agtctacttg cctcaagatg aattagcaca    3780
ggcaggtcta tccgatgaag atatatttgc tggaagggtg accgataaat ggagaatctt    3840
tatgaagaaa caaatacata gggcaagaaa gttctttgat gaggcagaga aaggcgtgac    3900
agaattgagc tcagctagta gattccctgt aagcattcgt aaactcttta gttttatgaa    3960
atgattcttt tttcgcgtta ttagatgaat atggttgctt gtgttgagta tttctaggtc    4020
gatgaagttg agacaagggt ttttaagttt taacgacttt tacggggtgc catgttatct    4080
gctacctaat cttaggtagt tgaccggaag ggctagaatt ttaacctcat gttcacccta    4140
ccaaccaaga aatgaacctc gcatagagct cgtagttatg aatatttgct ttggcatgac    4200
attgtgcgga tcatgaaatg tcttagatta tatggaaaaa tcattctatt acatcgaata    4260
gatacattag atctaagaag cacgccgtgt tgtaaatgag aaattctata gctcagatct    4320
ttagttttct ctgaacgacc tacaaaccaa cggataacct tgtattgagc ttgtcgttct    4380
cagtatttgc actaacatta cgtcgtgtgg atcctgaaat ggcttggatt gctattattc    4440
tggatatggc aaaaccattt tattagtact agatatcgaa taactacatt tgaccctaca    4500
agtaccctgg gttggagtta caatatccca tacctcgtat ctttagtgtt ctcttattta    4560
tcacctttgt ctactattct ggcaaaataa cctcactcgt tactcggtgt tttccaggta    4620
tgggcatctt tggtcttgta ccgcaaaata ctagatgaga ttgaagccaa tgactacaac    4680
aacttcacaa agagagcata tgtgagcaaa tcaaagaagt tgattgcatt acctattgca    4740
tatgcaaaat ctcttgtgcc tcctacaaaa actgcctctc ttcaaagata aagcatgaaa    4800
tgaagatata tatatatata tatatagcaa tatacattag aagaaaaaaa ggaagaagaa    4860
atgttgttgt attgatataa atgtatatca taaatattag gttgtagtaa cattcaatat    4920
aattatctct tgtagttgtt gtatcttcac tttatctc                           4958

<210> SEQ ID NO 7
<211> LENGTH: 22
<212> TYPE: DNA
<213> ORGANISM: Artificial sequence
<220> FEATURE:
<223> OTHER INFORMATION: Primer sequence

<400> SEQUENCE: 7
ggtggtggaa agcaaactaa ta                                              22

<210> SEQ ID NO 8
<211> LENGTH: 20
<212> TYPE: DNA
<213> ORGANISM: Artificial sequence
<220> FEATURE:
<223> OTHER INFORMATION: Primer sequence

<400> SEQUENCE: 8
tattaccccg gcagccttag                                                 20

<210> SEQ ID NO 9
<211> LENGTH: 735
<212> TYPE: DNA
<213> ORGANISM: Solanum pennellii

<400> SEQUENCE: 9
```

```
aggagatgac ctacgtacct ttttcacttt ggtaatatt cttatatttt ttgtttggga      60
atataattaa gttattattt ctatgatttt cataagcaaa gtaaaaagta ttttgtcctt    120
tttgtaaagg ttatggtgga ccctgatgct ccaagtccga gtgatccaaa tctgagagaa    180
taccttcact ggtccgtatt tttccttatt ctctcttctt tttaatctct ttcttttttg    240
accttttcac tttcccataa taattatatt ctttagtaat tatatatcct tttattttat    300
ttttaaaaat tggaaaggag aaacgaagag gagattttta catgtgaggg atttaattgt    360
aatgcaaatg gtagaaatat ataaatgtga agatatattc ttgaacttaa aaacaaacta    420
ctaaaataaa aatgaataaa atatttactc tgtcaatatt ctgtactata ttggtcaatg    480
aatatttata ttattcatga ctttaaaaat agtcaaaccg agacataagg taaaagtcaa    540
aatacgttta agctcattca tataaatgaa tatttttaaa ttttgttgca tccatcaaaa    600
tatctacttt ttaagaatga tatttatttt ataatattca tatttgattc gttgatggat    660
agattttatt ctgtaagaaa ttaaataaaa ataaaaattt aggcctagtc atatccatct    720
aaaatgggtg agatt                                                     735

<210> SEQ ID NO 10
<211> LENGTH: 706
<212> TYPE: DNA
<213> ORGANISM: Solanum lycopersicum

<400> SEQUENCE: 10
gaggagatga cctacgtacc tttttcactt tggtaatatt tcttatatt tttgtttggg      60 aatatagtta agttgatttt cataagcaaa gtaaaaagta ttttgtcctt tttgtaaagg    120
ttatggtgga ccctgatgct ccaagtccga gtgatccaaa tctgagagaa taccttcact    180
ggtccgtatt ttttccttat tctctcttct tttcatctct ttcttttttg acctttttac    240
ttaattatat tctttagtaa taatatgta tgatatcctt tttaaaaatt ggaaatacga    300
aaaggagaaa tgaagaggag atttacatgt gagggagcag atggtagaaa tatataaatg    360
tgaagatata tattcttgaa cttaaaaaca agctactaaa ataaaaatga ataaaatatt    420
tactctgtca atattctgta ctatattggt caatgaaatt ttatattatt catgacttta    480
aaaatagtca aacgagacat aacgtaaaag tcaaaatacg tttaagctca ttcatataaa    540
tgaatatttt taaatttgt tgcatccatc aaaatatcta cttttttaagg aatgatattt    600 atttcataat attcatattt gattcgttga tggatagatt ttattcttta aaaaattaaa    660
taaaaaaaat aaaattggcc tagtcatatc catctaaaat gggtga                   706

<210> SEQ ID NO 11
<211> LENGTH: 792
<212> TYPE: DNA
<213> ORGANISM: Solanum lycopersicum

<400> SEQUENCE: 11
tctggagaac ggacgatgac atcggaacag atggtctatg atgtggtttt gaggcaggca    60
gccttggtga agaggcaact gagatctacc aatgagttag aagtgaagcc ggatatacct    120
attccgggga atttgggctt gttgagtgaa gcatatgata ggtgtggtga agtatgtgca    180
gagtatgcaa agacgtttaa cttaggttag cttcttcaat ctattcattc gtttaccaaa    240
tattatttgg taagcactaa ttatgaatat atatatgttc atgttattga tgaagacaaa    300
atttgatctt tgtttgttta ttcaggaact atgctaatga ctcccgagag aagaagggct    360
atctgggcaa tatatggtga ggtttctagc catttaataa cagttacgcg cacaaacaca    420
```

```
tatgattaat cggggacgag aaaaaaagaa atgaagtttg agttttgagg gtcatatgta    480
ataggtaaat ccgagcttga ctagcttgag atgtttattg tcatatcatg ctcaatacta    540
accaaaacac tgaaaagaa cttgattata tttacatact aatattttca tttgcgttgc     600
tgttcacatt tttacctatg gaactggttt ttgtgatttg ttatacttca tattcgatgt    660
taataaaata tatcattcct cccttttttct ccacttcaag ctttactgta gtgttgaaag   720
gggaaactcc ttttaatgat tgcatatata aacgaacttc ttgagttgaa agttttctca   780
ttatgatctg tt                                                        792
```

<210> SEQ ID NO 12
<211> LENGTH: 836
<212> TYPE: DNA
<213> ORGANISM: Solanum lycopersicum

<400> SEQUENCE: 12

```
tctggtgaac ggacgatgac atcggaacag atggtctatg atgtggtttt gaggcaggca    60
gccttggtga agaggcagct gagatctacc aatgagttag aagtgaagcc ggatatacct   120
attccgggga atttgggctt gttgagtgaa gcatatgata ggtgtggtga agtatgtgca   180
gagtatgcaa agacgtttaa cttaggttag cttctttaat ctattcattt gtttaccaaa   240
tattatttgg taagcactaa ttatgactat atatatatat atatatatat atatatatat   300
atatatatct gttcatgtta ttgatgaaga caaaatttga tctttgtttg tttattcagg   360
aactatgcta atgactcccg agagaagaag ggctatctgg gcaatatatg gtgaggtttc   420 tagccatttta ataacagata cgcacacaaa cacatatgat taatcggaga cgagaaaaaa   480
agaaatgaag tttgagtttg agggtcatat ataataggta aatccgagct tgactagctt    540
gagatgttta ttgtcatatc atgctcaata ctaaccaaaa cactgaaaaa gaacatgatt   600
atatttacat actaatattt tcatttgcgt tgctgttcac atttttacct atggaactgg   660
ttttttttga tttgttatac ttcatattcg atgttaataa actatatcat tcctccctttt   720 ttctccactt caagctttac tgtagtgttg aaagggggaaa ctccttttaa tgattgcata   780
tataaacgaa cttcttgagt tgaaaaattt ctcattatga tctgttaaac agtatg       836
```

<210> SEQ ID NO 13
<211> LENGTH: 79
<212> TYPE: DNA
<213> ORGANISM: Artificial sequence
<220> FEATURE:
<223> OTHER INFORMATION: Consensus sequence

<400> SEQUENCE: 13

```
cctcttcrtt tctccctttt cgtatttcca attttttaaaa akraaatawm aksatatawa    60
ttactaaaga atataatta                                                 79
```

<210> SEQ ID NO 14
<211> LENGTH: 71
<212> TYPE: DNA
<213> ORGANISM: Solanum pennellii

<400> SEQUENCE: 14

```
cctcttcgtt tctccttttcc aattttttaaa aataaaataa aaggatatat aattactaaa    60
gaatataatt a                                                          71
```

<210> SEQ ID NO 15

```
<211> LENGTH: 77
<212> TYPE: DNA
<213> ORGANISM: Solanum lycopersicum

<400> SEQUENCE: 15
cctcttcatt tctccttttc gtatttccaa tttttaaaaa ggatatcatc atatattatt    60
actaaagaat ataatta                                                   77

<210> SEQ ID NO 16
<211> LENGTH: 20
<212> TYPE: DNA
<213> ORGANISM: Artificial sequence
<220> FEATURE:
<223> OTHER INFORMATION: Primer sequence

<400> SEQUENCE: 16
caagggttga agttggagga                                                20

<210> SEQ ID NO 17
<211> LENGTH: 20
<212> TYPE: DNA
<213> ORGANISM: Artificial sequence
<220> FEATURE:
<223> OTHER INFORMATION: Primer sequence

<400> SEQUENCE: 17
gacggtcagc gtaccagaat                                                20

<210> SEQ ID NO 18
<211> LENGTH: 24
<212> TYPE: DNA
<213> ORGANISM: Artificial sequence
<220> FEATURE:
<223> OTHER INFORMATION: Primer sequence

<400> SEQUENCE: 18
gaggtggtgg aaagcaaact aata                                           24

<210> SEQ ID NO 19
<211> LENGTH: 20
<212> TYPE: DNA
<213> ORGANISM: Artificial sequence
<220> FEATURE:
<223> OTHER INFORMATION: Primer sequence

<400> SEQUENCE: 19
ctaaggctgc cggggtaata                                                20
```